(12) United States Patent
Triebel et al.

(10) Patent No.: US 9,244,059 B2
(45) Date of Patent: Jan. 26, 2016

(54) CYTOTOXIC ANTI-LAG-3 MONOCLONAL ANTIBODY AND ITS USE IN THE TREATMENT OR PREVENTION OF ORGAN TRANSPLANT REJECTION AND AUTOIMMUNE DISEASE

(75) Inventors: Frederic Triebel, Versailles (FR); Bernard Vanhove, Reze (FR); Thomas Haudebourg, Nantes (FR)

(73) Assignees: Immutep Parc Club Orsay, Orsay (FR); Inserm—Institut National De La Sante Et De La Recherche Medicale, Paris (FR)

( * ) Notice: Subject to any disclaimer, the term of this patent is extended or adjusted under 35 U.S.C. 154(b) by 513 days.

(21) Appl. No.: 12/823,795

(22) Filed: Jun. 25, 2010

(65) Prior Publication Data

US 2011/0070238 A1 Mar. 24, 2011

Related U.S. Application Data

(63) Continuation-in-part of application No. 12/598,128, filed as application No. PCT/IB2008/001072 on Apr. 30, 2008.

(30) Foreign Application Priority Data

Apr. 30, 2007 (EP) .................................... 07290545

(51) Int. Cl.
*G01N 33/50* (2006.01)
*C07K 16/28* (2006.01)
*A61K 39/00* (2006.01)

(52) U.S. Cl.
CPC .......... *G01N 33/505* (2013.01); *C07K 16/2803* (2013.01); *A61K 2039/505* (2013.01); *C07K 2317/24* (2013.01); *C07K 2317/732* (2013.01); *C07K 2317/734* (2013.01); *C07K 2317/92* (2013.01); *G01N 2333/70503* (2013.01)

(58) Field of Classification Search
None
See application file for complete search history.

(56) References Cited

U.S. PATENT DOCUMENTS 5,976,877 A 11/1999 Hercend et al.

FOREIGN PATENT DOCUMENTS

| EP | 1158004 A | 5/2001 |
|---|---|---|
| EP | 1374902 A | 1/2004 |
| EP | 1987839 A1 | 11/2008 |
| WO | WO97/03695 A1 | 2/1997 |
| WO | WO99/15553 A2 | 4/1999 |
| WO | WO2004/078928 A2 | 9/2004 |
| WO | WO-2004078928 A2 | 9/2004 |
| WO | WO 2005/103086 A1 | 11/2005 |
| WO | WO2008/132601 A1 | 11/2008 |

OTHER PUBLICATIONS

D Pascalis, R., et al. J. Immunol. 2002;169:3076-3084.*
Lamminmaki, U., et al. J. Biol. Chem. 2001;276(39):36687-36694.*
André, et al., "CD40L stabilizes arrenal thrombi by a β3 integrin-dependent mechanism", *Nature Medicine*, vol. 8, No. 3, pp. 247-252 (2002).
Andreae, et al, "Maturation and Activation of Dendritic Cells Induced by Lymphocyte Activation Gene-3 (CD223)[1]", *The Journal of Immunology*, vol. 168, pp. 3874-3880 (2002).
Andreae, et al., "MHC class II signal transduction in human dendritic cells induced by a natural ligand, the LAG-3 protein (CD223)", *Blood*, vol. 102, No. 6, pp. 2130-2137 (2003).
Annunziato, et al., "Expression and release of LAG-3-encoded protein by human $CD4^+T$ cells are associated with IFN-γ production", *The FASEB Journal*, vol. 10, pp. 769-776 (1996).
Avice, et al al, "Lymphocyte Activation Gene-3, a MHC Class II Ligand Expressed on Activated T Cells, Stimulates TNF-α and IL-12 Production by Monocytes and Dendritic Cells[1]", *The Journal of Immunology*, vol. 162, pp. 2748-2753 (1999).
Bindon, et al , "Importance of antigen specificity for complement mediated lysis by monoclonal antibodies", *Eur J. Immunol.*, vol. 18, pp. 1507-1514 (1988).
Campbell, et al., "Collagen-induced arthritis in C57BL/6 ($H-2_b$) mice new insights into an important disease model of rheumatoid arthritis", *Eur. J. Immunol*, vol. 30, pp. 1568-1575 (2000).
Chan, et al., "Variable region domain exchange in human IgGs promotes antibody complex formation with accompanying structural changes and altered effector functions", *Molecular Immunology*, vol. 41, pp. 527-538 (2004).
Cole, et al, "The Ebv-Hybridoma Technique and its Application To Human Lung Cancer", *Monoclonal Antibodies and Cancer Therapy*, pp. 77-96 (1985).
Coles, at al., "*Alemtuzumab* vs. *Interferon Beta-1a in Early Multiple Sclerosis*", *The New England Journal of Medicine*, vol. 359, pp. 1786-1801 (2008).
Definition of auto-immunine, http://dictionary.cambridge.org/dictionary/british/auto-immune?=auto-immune Monday Jul. 30, 2012.
De Pascalis, et at., "Grafting of "Abbreviated" Complementarity-Determining Regions Containing Specificity-Determining Residues Essential for Ligand Contact to Engineer a Less Immunogenic Humanized Monoclonal Antibody", *The Journal of Inimunology*, vol. 169, pp. 3076-3084 (2002).

(Continued)

*Primary Examiner* — Gerald R Ewoldt
(74) *Attorney, Agent, or Firm* — Margaret M. Tomaska; Edward R. Gimmi

(57) ABSTRACT

Cytotoxic anti-LAG-3 monoclonal antibodies or fragments thereof causing depletion of $LAG-3^+$ activated T cells are described, as are related pharmaceuticals and methods of treating. Also described are related nucleic acid and protein sequences.

5 Claims, 18 Drawing Sheets

(56) References Cited

OTHER PUBLICATIONS

Drake, et al, "Blocking the regulatory T cell molecule LAG-3 augments in vivo anti-tumor immunity in an autochthonous model of prostate cancer", *Journal of Clinical Oncology*, vol. 24, No. 1SS, p. 2573 (2006).
Galli, et at., "Unequivocal Delayed Hypersensitivity in Mast Cell-Deficient and Beige Mice" Science, vol. 226, pp. 710-713 (1984).
Hargreaves, et al., "Selective depletion of activated T cells: the CD40L-specific antibody experience", *TRENDS in Molecular Medicine*, vol. 10, No. 3, pp. 130-135 (2004).
Haudebourg, et at, "Depletion of LAG-3 Positive Cells in Cardiac Allograft Reveals Their Role in Rejection and Tolerance", *Transplantation*, vol. 84, pp. 1500-1506 (2007).
Huang, of al, "Role of LAG-3 in Regulatory T Cells", *Immunity*, vol. 21, pp. 503-513, (2004).
Huard, et al., "LAG-3 does not define a specific mode of natural killing in human", *Immunology Letters*, vol. 61, pp. 109-112 (1998).
Huard, et al.,'"Lymphocyte-activation gene 3/major histocompatibility complex class II interaction modulates the antigenic response of CD4+ T lymphocytes", *Eur. J. Immunol*, vol. 24, pp. 3216-3221 (1994).
Inglis, et al., "Collagen-induced arthritis in C57BL/6 mice is associated with a robust and sustained T-cell response to type II collagen", *Arthritis Research & Therapy*, vol. 9, R113 (2007).
Issacs, J D , "From bench to bedside: discovering rules for antibody design, and improving serotherapy with monoclonal antibodies", *Rheumatology*, vol. 40, pp. 724-738 (2001).
lwai et al., "Invoivement of Inducible Costimulator-B7 Homologous Protein Costimulatory Pathway in Murine Lupus Nephritis1", *J. Immunol.*, vol. 171, pp. 2848-2854 (2003).
Kim, et al., "Antibody Engineering for the Development of Therapeutic Antibodies", *Mol. Cells*, vol. 20 No. 1, pp. 17-29 (2005).
Kisielow, et al, "Expression of lymphocyte activation gene 3 (LAG-3) on B cells is induced by T cells", *Eur J. Immunol.*, vol. 35, pp. 2081-2088 (2005).
Kohler, et al , "Continuous cultures of fused cells secreting antibody of predefined specificity", *Nature*, vol. 256, pp. 495-497 (1975).
Kunstfeld, et al., "Induction of cutaneous delayed-type hypersensitivity reactions in VEGF-A transgenic mice results in chronic skin inflammation associated with persistent lymphatic hyperplasia", *Blood*, vol. 104, pp. 1048-1057 (2004).
Lamminmaki, at al., "Crystal Structure of a Recombinant Anti-estradiol Fab Fragment in Complex with 17β-Estradiol", *The Journal of Biological Chemistry*, vol. 276, No. 39, pp. 36687-36694 (2001).
Lange-Asschenfeldt, at al, "lncreased and prolonged inflammation and angiogenesis in delayed-type hypersensitivity reactions elicited in the skin of thrombospondin-2-deficient mice", *Blood*, vol. 99 pp. 538-545 (2002).
Macon-Lemaitre, at al., "The negative regulatory function of the Lymphocyte-activation geneoo3 co~receptor (CD223) on human T cells", *Immunology*, vol. 115, No. 2, pages 170-178 (2005).

Mages, at al., "Molecular cloning and characterization of murine ICOS and identification of B7h as ICOS ligand", *Eur. J. Immunol*, vol. 30, pp. 1040-1047 (2000).
Monk, at al., "Fe-dependent depletion of activated T cells occurs through CD40L-specific antibody rather than costimulation blockade", *Nature Medicine*, vol. 9, No. 10, pp. 1275-1280 (2003).
Nishida, at al., "Novel humanized anti-CD20 monoclonal antibodies with unique germline VH and VL gene recruitment and potent effector functions" International *Journal of Oncology*, vol. 32, pp. 1263-1274 (2008).
Nobel Jamieson, et al., "Auto-immune cholangiopathy in a juvenile patient with systemic lupus erythematosus", *Acta Paediatrica*, Foundation Acta Paediatrica, 101,e262-264 (2012).
Ono, et al., "lllIproved technique of heart transplantation in rats", *Journal of Thoracic and Cardiovascular Surgery*, vol. 57, No. 2, pp. 225-229 (1969).
Ozkaynak, at al., "Importance of ICOS-B7RP-1 costimulation in acute and chronic allograft rejection" *Nature Immunology*, vol. 2, No. 7, pp. 591-596 (2001).
Saito, et al., "A Tumor Necrosis Factor Receptor Loop Peptide Mimic Inhibits Bone Destruction to the Same Extent as Anti-Tumor Necrosis Factor Monoclonal Antibody in Murine Collagen-Induced Arthritis", *Arthritis & Rheumatism*, vol. 56, No, 4, pp. 1164-1174 (2007).
Sakamoto, et al., "AILIM/ICOS: Its Expression and Functional Analysis with Monoclonal Antibodies", Hybridoma and Hybridomics, vol. 20, No. 5, pp. 293-303 (2001).
Song, et at., "Rat and Human Natural Killers Exhibit Contrasting Immunoglobulin G Subclass Specificities in Anti body-Dependent Cellular Cytotoxicity Reflecting Differences in Their Fc Receptors (FcγR)", *Journal of Leukocyte Biology*, vol. 48, pp. 524-530 (1990).
Sporici, et al., "ICOS Ligand Costimulation Is Required for T-Cell Encephalitogenicity", *Clinical Immunology*, vol. 100, No. 3, pp. 277-288 (2001).
Stasiuk, et al, "Collagen-Induced Arthritis in DBA/1 Mice: Cytokine Gene Activation Following Immunization with Type II Collagen", *Cellular Immunology*, vol. 173, pp. 269-275 (1996).
Teeling, et al., "The Biological Activity of Human CD20 Monoclonal Antibodies Is Linked to Unique Epitopes on CD201", *The Journal of Immunology*, vol. 177, pp. 362-371 (2006).
Totsuka, et al., "Ameliorating Effect of Anti-inducible Castimulator Monoclonal Antibody in a Murine Model of Chronic Colitis", *Gastroenterology*, vol. 124, pp. 410-421 (2003).
Triebel, et at., "LAG-3: a regulator of T-cell and DC responses and its use in therapeutic vaccination", TRENDS in Immunology, vol. 24, No. 12, pp. 619-622 (2003).
Virella, et al , "Biosynthesis, Metabolism, and Biological Properties", Introduction to Medical Immunology, Chapter 6, 4th Edition pp. 99-100 (1998).
Waldmann, Herman, "The new immunosuppression: just kill the T cell", *Nature Medicine*, vol. 9, No. 10, pp. 1259-1260 (2003).
Yousaf, et al., "Targeting behavior of rat monoclonal IgG antibodies in vivo. role of antibody isotype, specificity and the target cell antigen density", *Eur. J. Immunol.*, vol. 21, pp. 943-950 (1991).

\* cited by examiner

A
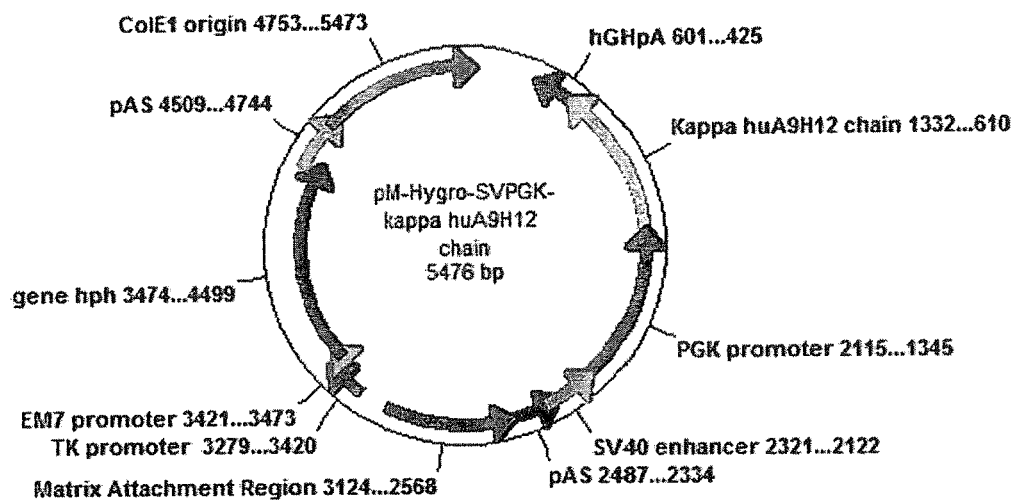
B
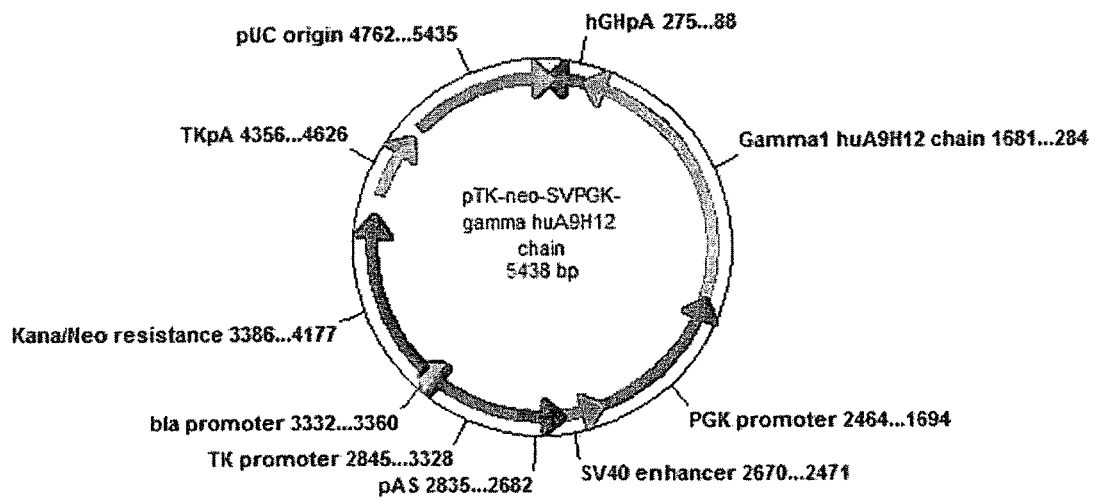
Figure 11

A
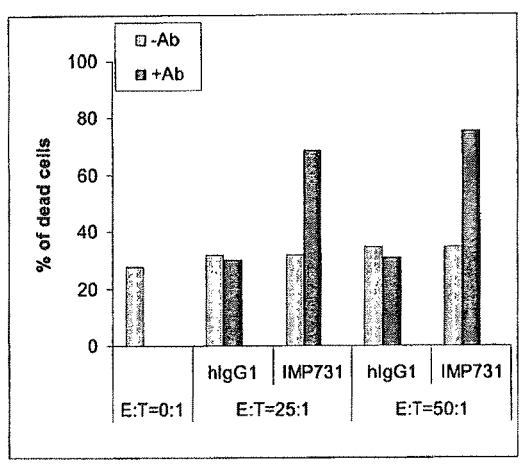
B
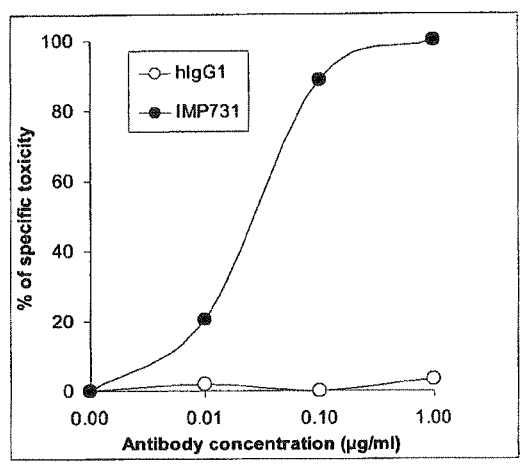
C
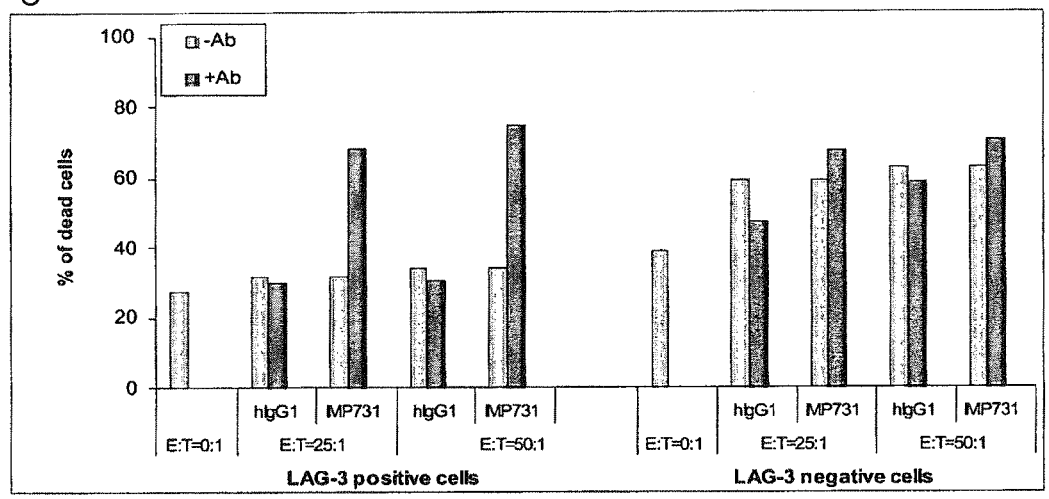
Figure 15

Figure 16
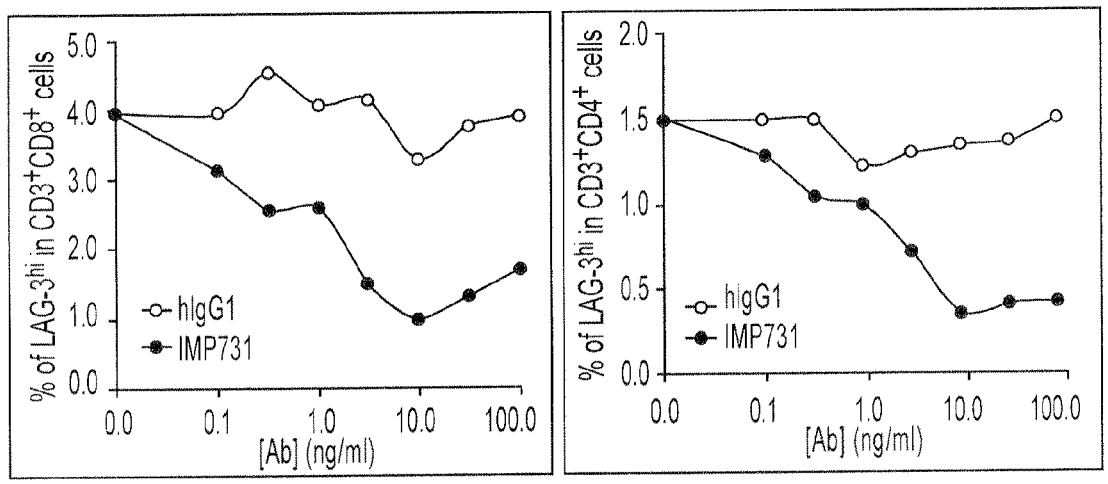
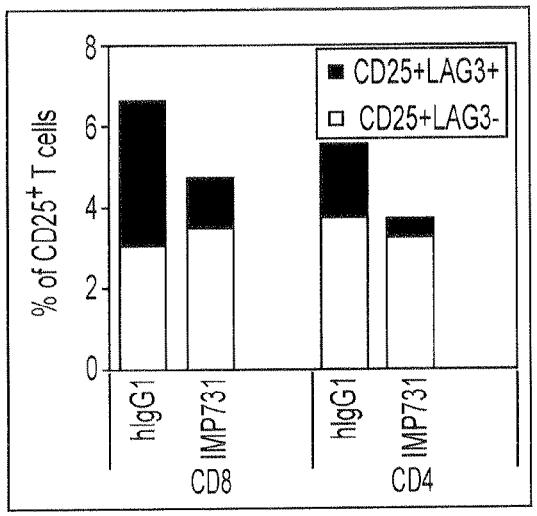

Figure 20

IMP731 kappa DNA sequence
ATGGAATCACAGACCCAGGTCCTCATGTTTCTTCTGCTCTGGGTATCTGGTGCCTGTGCAGACAT
TGTGATGACACAGTCTCCCTCCTCCCTGGCTGTGTCAGTAGGACAGAAGGTCACTATGAGCTGC
AAGTCCAGTCAGAGCCTTTTAAATGGTAGCAATCAAAAGAACTACTTGGCCTGGTACCAGCAGAA
ACCAGGACAGTCTCCTAAACTTCTGGTATACTTTGCATCCACTAGGGATTCTGGGGTCCCTGATC
GCTTCATAGGCAGTGGATCTGGGACAGATTTCACTCTTACCATCAGCAGTGTGCAGGCTGAAGA
CCTGGCAGATTACTTCTGTCTGCAACATTTTGGCACTCCTCCGACGTTCGGTGGAGGCACCAAA
CTGGAAATCAAACGGACCGTGGCTGCACCATCTGTCTTCATCTTCCCGCCATCTGATGAGCAGTT
GAAATCTGGAACTGCCTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTCACAGAGCAGGACA
GCAAGGACAGCACCTACAGCCTCAGCAGCACCCTGACGCTGAGCAAAGCAGACTACGAGAAAC
ACAAAGTCTACGCCTGCGAAGTCACCCATCAGGGCCTGAGTTCGCCCGTCACAAAGAGCTTCAA
CAGGGGAGAGTGTTAA

IMP731 kappa amino acid sequence
Signal peptide                            Variable region
M E S Q T Q V L M F L L L W V S G A C A D I V M T Q S P S S L A V S V G Q K V T M S C K S S Q
S L L N G S N Q K N Y L A W Y Q Q K P G Q S P K L L V Y F A S T R D S G V P D R F I G S G S G
T D F T L T I S S V Q A E D L A D Y F C L Q H F G T P P T F G G G T K L E I K R T V A A P S V F I
F P P S D E Q L K S G T A S V V C L L N N F Y P R E A K V Q W K V D N A L Q S G N S Q E S V T
E Q D S K D S T Y S L S S T L T L S K A D Y E K H K V Y A C E V T H Q G L S S P V T K S F N R
G E C Stop
Constant region

IMP731 variable kappa light chain DNA sequence
GACATTGTGATGACACAGTCTCCCTCCTCCCTGGCTGTGTCAGTAGGACAGAAGGTCACTATGA
GCTGCAAGTCCAGTCAGAGCCTTTTAAATGGTAGCAATCAAAAGAACTACTTGGCCTGGTACCAG
CAGAAACCAGGACAGTCTCCTAAACTTCTGGTATACTTTGCATCCACTAGGGATTCTGGGGTCCC
TGATCGCTTCATAGGCAGTGGATCTGGGACAGATTTCACTCTTACCATCAGCAGTGTGCAGGCT
GAAGACCTGGCAGATTACTTCTGTCTGCAACATTTTGGCACTCCTCCGACGTTCGGTGGAGGCA
CCAAACTGGAAATCAAACGG

IMP731 variable kappa light chain protein sequence
D I V M T Q S P S S L A V S V G Q K V T M S C K S S Q S L L N G S N Q K N Y L A W Y Q Q K P G
Q S P K L L V Y F A S T R D S G V P D R F I G S G S G T D F T L T I S S V Q A E D L A D Y F C L
Q H F G T P P T F G G G T K L E I K R

CDR-L1: QSLLNGSNQKNY

CDR-L2: FAS

CDR-L3: LQHFGTPPT

Figure 21

IMP 731 gamma DNA sequence
ATGGCTGTCTTGGGGCTGCTCTTCTGCCTGGTAACATTCCCAAGCTGTATCCTTTCCcaggtgcagct
gaaggagtcaggtcctggcctggtggcgccctcacagagcctgtccatcacatgcaccgtctcagggttctcattaaccgcctatggtgtaaact
gggttcgccagcctccaggaaagggtctggagtggctgggaatgatatgggatgatggaagcacagactataattcagctctcaaatccaga
ctgagcatcagtaaggacaactccaagagccaagtttcttaaaaatgaacagtctgcaaactgatgacacagccaggtactactgtgccag
agaaggggacgtagcctttgactactggggccaaggcaccactctcacagtctcctcagctagcACCAAGGGCCCATCGGTCT
TCCCCCTGGCACCCTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTGACCAGCGGCGTGC
ACACCTTCCCGGCTGTCCTACAGTCCTCAGGACTCTACTCCCTCAGCAGCGTGGTGACCGTGCC
CTCCAGCAGCTTGGGCACCCAGACCTACATCTGCAACGTGAATCACAAGCCCAGCAACACCAAG
GTGGACAAGAAAGttGAGCCCAAATCTTGTGACAAAACTCACACATGCCCACCGTGCCCAGCACC
TGAACTCCTGGGGGGACCGTCAGTCTTCCTCTTCCCCCCAAAACCCAAGGACACCCTCATGATC
TCCCGGACCCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGGAGGAGCAG
TACAACAGCACGTACCGtGTGGTCAGCGTCCTCACCGTCCTGCACCAGGACTGGCTGAATGGCA
AGGAGTACAAGTGCAAGGTCTCCAACAAAGCCCTCCCAGCCCCCATCGAGAAAACCATCTCCAA
AGCCAAAGGGCAGCCCCGAGAACCACAGGTGTACACCCTGCCCCCATCCCGGGATGAGCTGacc
AAGAACCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCTCCCTGTCT
CCGGGTAAATAA

IMP 731 gamma amino acid sequence
Signal peptide                          Variable region
M A V L G L L F C L V T F P S C I L S Q V Q L K E S G P G L V A P S Q S L S I T C T V S G F S L T
A Y G V N W V R Q P P G K G L E W L G M I W D D G S T D Y N S A L K S R L S I S K D N S K S Q
V F L K M N S L Q T D D T A R Y Y C A R E G D V A F D Y W G Q G T T L T V S S A S T K G P S V
F P L A P S S K S T S G G T A A L G C L V K D Y F P E P V T V S W N S G A L T S G V H T F P A
V L Q S S G L Y S L S S V V T V P S S S L G T Q T Y I C N V N H K P S N T K V D K K V E P K S C
D K T H T C P P C P A P E L L G G P S V F L F P P K P K D T L M I S R T P E V T C V V V D V S H
E D P E V K F N W Y V D G V E V H N A K T K P R E E Q Y N S T Y R V V S V L T V L H Q D W L N
G K E Y K C K V S N K A L P A P I E K T I S K A K G Q P R E P Q V Y T L P P S R D E L T K N Q V
S L T C L V K G F Y P S D I A V E W E S N G Q P E N N Y K T T P P V L D S D G S F F L Y S K L T
V D K S R W Q Q G N V F S C S V M H E A L H N H Y T Q K S L S L S P G K Stop
        Constant region

IMP731 variable gamma heavy chain DNA sequence
CAGGTGCAGCTGAAGGAGTCAGGTCCTGGCCTGGTGGCGCCCTCACAGAGCCTGTCCATCACA
TGCACCGTCTCAGGGTTCTCATTAACCGCCTATGGTGTAAACTGGGTTCGCCAGCCTCCAGGAA
AGGGTCTGGAGTGGCTGGGAATGATATGGGATGATGGAAGCACAGACTATAATTCAGCTCTCAA
ATCCAGACTGAGCATCAGTAAGGACAACTCCAAGAGCCAAGTTTTCTTAAAAATGAACAGTCTGC
AAACTGATGACACAGCCAGGTACTACTGTGCCAGAGAAGGGGACGTAGCCTTTGACTACTGGGG
CCAAGGCACCACTCTCACAGTCTCCTCA

IMP731 variable gamma heavy chain protein sequence
Q V Q L K E S G P G L V A P S Q S L S I T C T V S G F S L T A Y G V N W V R Q P P G K
G L E W L G M I W D D G S T D Y N S A L K S R L S I S K D N S K S Q V F L K M N S L Q
T D D T A R Y Y C A R E G D V A F D Y W G Q G T T L T V S S

CDR-H1: GFSLTAYG
CDR-H2: IWDDGST
CDR-H3: AREGDVAFDY

SEQUENCE LISTING

```
<160> NUMBER OF SEQ ID NOS: 25

<210> SEQ ID NO 1
<211> LENGTH: 25
<212> TYPE: PRT
<213> ORGANISM: Rattus norvegicus

<400> SEQUENCE: 1

Asp Gln Pro Ala Ser Ile Pro Ala Leu Asp Leu Leu Gln Gly Met Pro
1               5                   10                  15

Ser Thr Arg Arg His Pro Pro His Arg
            20                  25

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atatgaattc acagaggaga tgaggcag                                            28
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atatgaattc tcctggtcag agctgcct                                      28

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggatgctat ggaaggaaag a                                             21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gattctggtg acagctggtg                                               20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccttggtcaa gcagtacagc c                                             21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttcgctgatg acacaaacat ga                                            22

<210> SEQ ID NO 8
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 8

-continued

```
gac att gtg atg aca cag tct ccc tcc tcc ctg gct gtg tca gta gga      48
Asp Ile Val Met Thr Gln Ser Pro Ser Ser Leu Ala Val Ser Val Gly
1               5                   10                  15 cag aag gtc act atg agc tgc aag tcc agt cag agc ctt tta aat ggt      96
Gln Lys Val Thr Met Ser Cys Lys Ser Ser Gln Ser Leu Leu Asn Gly
            20                  25                  30 agc aat caa aag aac tac ttg gcc tgg tac cag cag aaa cca gga cag     144
Ser Asn Gln Lys Asn Tyr Leu Ala Trp Tyr Gln Gln Lys Pro Gly Gln
        35                  40                  45 tct cct aaa ctt ctg gta tac ttt gca tcc act agg gat tct ggg gtc     192
Ser Pro Lys Leu Leu Val Tyr Phe Ala Ser Thr Arg Asp Ser Gly Val
    50                  55                  60 cct gat cgc ttc ata ggc agt gga tct ggg aca gat ttc act ctt acc     240
Pro Asp Arg Phe Ile Gly Ser Gly Ser Gly Thr Asp Phe Thr Leu Thr
65                  70                  75                  80 atc agc agt gtg cag gct gaa gac ctg gca gat tac ttc tgt ctg caa     288
Ile Ser Ser Val Gln Ala Glu Asp Leu Ala Asp Tyr Phe Cys Leu Gln
                85                  90                  95 cat ttt ggc act cct ccg acg ttc ggt gga ggc acc aaa ctg gaa atc     336
His Phe Gly Thr Pro Pro Thr Phe Gly Gly Gly Thr Lys Leu Glu Ile
            100                 105                 110 aaa cgg                                                             342
Lys Arg
```

<210> SEQ ID NO 9
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Ser Pro Lys Leu Leu Val Tyr Phe Ala Ser Thr Arg Asp Ser Gly
1               5                   10                  15

Val Pro Asp Arg Phe Ile Gly Ser Gly Ser Gly Thr Asp Phe Thr Leu
            20                  25                  30

Thr Ile Ser Ser Val Gln Ala Glu Asp Leu Ala Asp Tyr Phe Cys Leu
        35                  40                  45

Gln His Phe Gly Thr Pro Pro Thr Phe Gly Gly Gly Thr Lys Leu Glu
    50                  55                  60

Ile Lys Arg
65
```

<210> SEQ ID NO 10
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(348)

<400> SEQUENCE: 10

```
cag gtg cag ctg aag gag tca ggt cct ggc ctg gtg gcg ccc tca cag      48
Gln Val Gln Leu Lys Glu Ser Gly Pro Gly Leu Val Ala Pro Ser Gln
1               5                   10                  15 agc ctg tcc atc aca tgc acc gtc tca ggg ttc tca tta acc gcc tat      96
Ser Leu Ser Ile Thr Cys Thr Val Ser Gly Phe Ser Leu Thr Ala Tyr
            20                  25                  30
```

```
ggt gta aac tgg gtt cgc cag cct cca gga aag ggt ctg gag tgg ctg      144
Gly Val Asn Trp Val Arg Gln Pro Pro Gly Lys Gly Leu Glu Trp Leu
        35                  40                  45 gga atg ata tgg gat gat gga agc aca gac tat aat tca gct ctc aaa      192
Gly Met Ile Trp Asp Asp Gly Ser Thr Asp Tyr Asn Ser Ala Leu Lys
 50                  55                  60 tcc aga ctg agc atc agt aag gac aac tcc aag agc caa gtt ttc tta      240
Ser Arg Leu Ser Ile Ser Lys Asp Asn Ser Lys Ser Gln Val Phe Leu
 65                  70                  75                  80 aaa atg aac agt ctg caa act gat gac aca gcc agg tac tac tgt gcc      288
Lys Met Asn Ser Leu Gln Thr Asp Asp Thr Ala Arg Tyr Tyr Cys Ala
                 85                  90                  95 aga gaa ggg gac gta gcc ttt gac tac tgg ggc caa ggc acc act ctc      336
Arg Glu Gly Asp Val Ala Phe Asp Tyr Trp Gly Gln Gly Thr Thr Leu
                100                 105                 110 aca gtc tcc tca                                                      348
Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ala Tyr
             20                  25                  30

Gly Val Asn Trp Val Arg Gln Pro Pro Gly Lys Gly Leu Glu Trp Leu
         35                  40                  45

Gly Met Ile Trp Asp Asp Gly Ser Thr Asp Tyr Asn Ser Ala Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Arg Glu Gly Asp Val Ala Phe Asp Tyr Trp Gly Gln Gly Thr Thr Leu
                100                 105                 110

Thr Val Ser Ser
        115

<210> SEQ ID NO 12
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggaatcac agacccaggt cctcatgttt cttctgctct ggtatctggg tgcctgtgca      60
gacattgtga tgacacagtc tcctcctcc ctggctgtgt cagtaggaca gaaggtcact     120
atgagctgca agtccagtca gagccttta aatggtagca atcaaaagaa ctacttggcc     180
tggtaccagc agaaaccagg acagtctcct aaacttctgg tatactttgc atccactagg    240
```

```
gattctgggg tccctgatcg cttcataggc agtggatctg ggacagattt cactcttacc    300
atcagcagtg tgcaggctga agacctggca gattacttct gtctgcaaca ttttggcact    360
cctccgacgt tcggtggagg caccaaactg gaaatcaaac ggaccgtggc tgcaccatct    420
gtcttcatct cccgccatc tgatgagcag ttgaaatctg gaactgcctc tgttgtgtgc     480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagttcgccc gtcacaaaga gcttcaacag gggagagtgt    720
taa                                                                  723
```

```
<210> SEQ ID NO 13
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

```
Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Val Ser Val Gly Gln Lys Val Thr Met Ser Cys Lys Ser Ser Gln Ser
        35                  40                  45

Leu Leu Asn Gly Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Asp Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Leu Gln His Phe Gly Thr Pro Pro Thr Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

```
<210> SEQ ID NO 14
<211> LENGTH: 114
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 14

```
Asp Ile Val Met Thr Gln Ser Pro Ser Leu Ala Val Ser Val Gly
1               5                  10                  15

Gln Lys Val Thr Met Ser Cys Lys Ser Ser Gln Ser Leu Leu Asn Gly
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Leu Gln
                85                  90                  95

His Phe Gly Thr Pro Pro Thr Phe Gly Gly Gly Thr Lys Leu Glu Ile
            100                 105                 110

Lys Arg
```

<210> SEQ ID NO 15
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atggctgtct tggggctgct cttctgcctg gtaacattcc caagctgtat cctttcccag     60
gtgcagctga aggagtcagg tcctggcctg gtggcgccct cacagagcct gtccatcaca    120
tgcaccgtct cagggttctc attaaccgcc tatggtgtaa actgggttcg ccagcctcca    180
ggaaagggtc tggagtggct gggaatgata tgggatgatg aagcacaga ctataattca     240
gctctcaaat ccagactgag catcagtaag acaactcca agagccaagt tttcttaaaa     300
atgaacagtc tgcaaactga tgacacagcc aggtactact gtgccagaga aggggacgta    360
gcctttgact actgggggcca aggcaccact ctcacagtct cctcagctag caccaagggc    420
ccatcggtct tccccctggc accctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac acaggtgta cccctgcccc catcccggg atgagctgac caagaaccag    1140
gtcagcctga cctgcctggt caaaggcttc tatcccagcg acatcgccgt ggagtgggag   1200
```

-continued

```
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaataa                                                   1398
```

<210> SEQ ID NO 16
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Ala Val Leu Gly Leu Leu Phe Cys Leu Val Thr Phe Pro Ser Cys
 1               5                  10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asn Trp Val Arg Gln Pro Pro Gly Lys Gly Leu
    50                  55                  60

Glu Trp Leu Gly Met Ile Trp Asp Asp Gly Ser Thr Asp Tyr Asn Ser
65                  70                  75                  80

Ala Leu Lys Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Arg Tyr
            100                 105                 110

Tyr Cys Ala Arg Glu Gly Asp Val Ala Phe Asp Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320
```

```
Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ser Leu Leu Asn Gly Ser Asn Gln Lys Asn Tyr
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gln His Phe Gly Thr Pro Pro Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Ser Leu Thr Ala Tyr Gly
1               5

<210> SEQ ID NO 20
<211> LENGTH: 7
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 20

Ile Trp Asp Asp Gly Ser Thr
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 21

Ala Arg Glu Gly Asp Val Ala Phe Asp Tyr
1               5                   10

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: CDS
<222> LOCATION: (1)..(60)

<400> SEQUENCE: 22 atg gaa tca cag acc cag gtc ctc atg ttt ctt ctg ctc tgg gta tct       48
Met Glu Ser Gln Thr Gln Val Leu Met Phe Leu Leu Leu Trp Val Ser
1               5                   10                  15 ggt gcc tgt gca                                                       60
Gly Ala Cys Ala
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 23

Met Glu Ser Gln Thr Gln Val Leu Met Phe Leu Leu Leu Trp Val Ser
1               5                   10                  15

Gly Ala Cys Ala
            20

<210> SEQ ID NO 24
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: CDS
<222> LOCATION: (1)..(57)

<400> SEQUENCE: 24 atg gct gtc ttg ggg ctg ctc ttc tgc ctg gta aca ttc cca agc tgt       48
Met Ala Val Leu Gly Leu Leu Phe Cys Leu Val Thr Phe Pro Ser Cys
1               5                   10                  15

```
atc ctt tcc                                                     57
Ile Leu Ser <210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Ala Val Leu Gly Leu Leu Phe Cys Leu Val Thr Phe Pro Ser Cys
1               5                   10                  15

Ile Leu Ser
```

US 9,244,059 B2

CYTOTOXIC ANTI-LAG-3 MONOCLONAL ANTIBODY AND ITS USE IN THE TREATMENT OR PREVENTION OF ORGAN TRANSPLANT REJECTION AND AUTOIMMUNE DISEASE

CROSS-REFERENCE TO RELATED APPLICATION

This application is a Continuation-in-part application of U.S. application Ser. No. 12/598,128, which was filed Oct. 29, 2009 and which is a National Stage entry of International Application No. PCT/IB/2008/001072, filed Apr. 30, 2008, which claims priority to European Patent Application No. 07290545.8, filed Apr. 30, 2007, the disclosures of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 12, 2010, is named 21305323.txt and is 21,733 bytes in size.

I. FIELD OF THE INVENTION

The present invention is in the field of immunotherapy. More specifically, it relates to the treatment or prevention of organ transplant rejection or for treating autoimmune disease. The invention relates to molecule binding to LAG-3 protein and causing depletion of LAG-3$^+$ activated T cells. More specifically, it relates to cytotoxic LAG-3-specific monoclonal antibody or fragment thereof.

II. BACKGROUND

Lymphocyte activation gene-3 (LAG-3, CD223) is upregulated during the early stages of T-cell activation. The present invention is based on the analysis of the effects of cytotoxic antibodies against LAG-3 in acute cardiac allograft rejection (in vivo animal studies) and in in vitro experiments where selected LAG-3 monoclonal antibodies are efficient at low doses (<0.1 µg/ml) at depleting LAG-3$^+$ activated effector T cells.

Selectively depleting activated T lymphocytes might represent an immunosuppressive induction treatment able to result in the development of regulatory cells supporting a long-term survival of allogeneic organs in mice and primates (1). This has actually been demonstrated with anti-CD40L antibodies that deplete in vivo activated T cells through a Fc-dependent mechanism (2). However, anti-CD40L antibodies also target activated platelets in humans and affect the stability of arterial thrombi (3). Therefore the development of monoclonal antibodies to other molecules specific for T-cell activation has catalyzed attempts to achieve immunosuppression. One such molecule is LAG-3, which engages Class II on dendritic cells (DC) with a high affinity, enabling DC to become activated (4-6). The LAG-3 protein is expressed in vivo in activated CD4$^+$ and CD8$^+$ lymphocytes residing in inflamed secondary lymphoid organs or tissues but not in spleen, thymus or blood (7). In addition, LAG-3 can function as a negative regulator of activated human CD4 and CD8 T cells by inhibiting early events in primary activation (8).

III. SUMMARY OF THE INVENTION

The invention provides a molecule binding to LAG-3 protein and causing depletion of LAG-3$^+$ activated T cells. Said depletion can be measured by changes in peripheral blood lymphocyte numbers, in a tissue or an organ.

In a preferred embodiment the molecule binding to LAG-3 protein is a cytotoxic anti-LAG-3 monoclonal antibody or fragment thereof causing depletion of LAG-3$^+$ activated T cells, said antibody comprising an Fc fragment from the human IgG1 or IgM (or mouse IgG2a) subclass and an Fab fragment which binds LAG-3 protein, said antibody exhibiting a complement-dependant cytotoxicity (CDC) and/or an antibody dependant cell cytotoxicity activity (ADCC).

In one embodiment, the anti-LAG-3 monoclonal antibody is IMP731 or a biologically active fragment thereof.

Another aspect of the invention is a method of depleting LAG-3$^+$ activated T cells in a mammal, the method comprising administering monoclonal antibody IMP731 or a biologically active fragment thereof to said mammal.

Another embodiment of the invention is a pharmaceutical composition comprising monoclonal antibody IMP731 or a biologically active fragment thereof.

Another embodiment of the invention is a method of treating diseases associated with LAG-3$^+$ activated T cells in a subject, the method comprising administering an effective amount of a pharmaceutical composition comprising monoclonal antibody IMP731 or a biologically active fragment thereof to said subject. Such disease may be an auto-immune disease. Exemplary auto-immune diseases include autoimmune hemolytic anemia, autoimmune thrombocytopenia purpura, Goodpasture's syndrome, pemphigus vulgaris, acute rheumatic fever, mixed essential cryoglobulinemia, systemic lupus erythematosus, insulin-dependent diabetes mellitus, rheumatoid arthritis, Grave's disease, Hashimoto's thyroiditis, myasthenia gravis, psoriasis and multiple sclerosis.

The present invention further provides a method for treating or preventing organ transplant rejection or for treating auto-immune disease. Said method comprises the administration, to a mammalian subject, of a therapeutically effective amount of a cytotoxic anti-LAG-3 monoclonal antibody or fragment thereof. In one embodiment, the monoclonal antibody is IMP731.

Another embodiment of the invention is directed to an isolated nucleic acid molecule comprising a nucleic acid sequence encoding the kappa region of IMP731 or a biologically active fragment thereof.

Another embodiment is directed to a polypeptide encoded by a nucleic acid molecule comprising a nucleic acid sequence encoding the kappa region of IMP731 or a biologically active fragment thereof.

Another embodiment is directed to an isolated nucleic acid molecule comprising a nucleic acid sequence encoding the gamma region of IMP731 or a biologically active fragment thereof.

Another embodiment is directed to a polypeptide encoded by nucleic acid molecule comprising a nucleic acid sequence encoding the gamma region of IMP731 or a biologically active fragment thereof.

Another embodiment is directed to an antibody that binds LAG-3 protein and depletes LAG-3$^+$ activated T cells and comprises a light chain variable region comprising the 3 CDRs in FIG. 22 and a heavy chain variable region comprising the 3 CDR's in FIG. 23.

Another embodiment of the invention is directed to a method of identifying a molecule that binds LAG-3 protein and may deplete LAG-3$^+$ activated T cells, the method comprising providing an assay in which a candidate molecule and IMP371 compete for binding on an LAG-3 protein, wherein when said candidate blocks IMP371 from binding said LAG-3 protein, said candidate is identified as a molecule that binds LAG-3 protein and may deplete LAG-3$^+$ activated T cells.

Another embodiment of the invention is directed to a method of assessing a candidate molecule for cytotoxicity on LAG-3$^+$ activated T cells, the method comprising incubating T-cells in a CMV peptide containing medium with the candidate molecule and under the same conditions, incubating T-cells in a CMV peptide containing medium without the candidate molecule and comparing the percentage of T cells expressing an activation marker with the candidate molecule against the percentage of T cells expressing an activation markers without the candidate molecule, wherein a reduction in the percentage of activated T-cells with the candidate molecule indicates the cytotoxicity of the candidate molecule on LAG-3$^+$ activated T cells.

IV. DESCRIPTION OF THE FIGURES

FIG. 1: LAG-3 mRNA expression in cardiac allograft (A), in the spleen (B) and in lymph nodes (C). Expression of LAG-3 mRNA in heart grafts at day 5 was measured by quantitative RT-PCR and compared with housekeeping HPRT transcripts expression. Rejection: allograft without treatment. Syngenic: isograft. Tolerant: allograft in recipients receiving a tolerogenic (CsA+anti-CD28 antibodies) treatment. **: $p<0.05$ for syngenic and tolerant vs. rejection.

FIG. 2: Characterization of anti-LAG-3 antibodies in a complement-dependant cytotoxicity assay. ConA-stimulated target cells were labeled with $^{51}$Cr and mixed with rabbit complement and anti-LAG-3 (full line) or preimmune (dotted line) serum at the indicated dilution. % cytotoxic activity is calculated as follows: (CPM of the assay−spontaneous CPM release)/maximum released CPM obtained after cell lysis.

FIG. 3: In vitro depleting activity of anti-LAG-3 antibodies. T cells from the spleen were activated for 48 h with Con A to induce expression of LAG-3 and labeled with CFSE. $10^5$ cells were injected i.v. to recipients that had been irradiated (4.5 Gy) 3 days before. Twenty-four hours after injection, recipients were sacrificed and the presence of CD4$^+$ cells in the CD8$^+$ and CD8' compartments of the spleen analyzed by flow cytometry.

FIG. 4: Heart graft survival after anti-LAG-3 antibodies administration. Lew.IA recipients of fully allogeneic (class I and II mismatch) Lew.1W hearts were treated by injections on days 0 and 3 of 200 µl (dashed line) or 600 µl (full line) rabbit anti-LAG-3 serum or of 600 µl pre-immune serum (dotted line). Graft survival was evaluated by daily evaluation of heartbeat. $P<0.002$ for 600 µl rabbit anti-LAG-3 serum vs. pre-immune serum.

FIG. 5: Analysis of Graft infiltrating cells (GICs). GICs were extracted from cardiac allografts on day 5 from control-treated or anti-LAG-3 antibodies treated recipients. Cells were counted and analyzed by flow cytometry for the expression of LAG-3. White bars: total number of GICs. Black bars: LAG-3$^+$ GICs measured by flow cytometry ($p<0.01$). Total RNA was also extracted from GICs and messenger for INFγ were quantified by qPCR, relative to HPRT expression level (dashed bars; $p<0.05$).

FIG. 6: Comparison of A9H12 binding with the reference LAG-3 specific 17B4 mAb on LAG-3$^+$ CHO and activated human T cells.

A) hLAG-3-transfected CHO were dissociated from culture plastic using Versene buffer containing cation-chelating agent, incubated with indicated concentrations of A9H12 or 17B4 mAbs for 30 min at 40 C, washed and then incubated with a FITC-conjugated goat anti-mouse IgG+M (H+L) secondary antibody (5 µg/ml, Coulter Inc.) for 30 minutes at 4° C. After washing, cells were analysed by flow cytometry using a FACSCanto™ (BD Biosciences) and means of fluorescence intensity were plotted as a function of antibody concentration.

B) PBMCs from a healthy volunteer were stimulated for 2 days with SEB (1 µg/ml, Sigma Aldrich) to induce the expression of LAG-3 on T cells. PBMCs were stained as above. Data represent a weighted percentage, calculated as the percentage of LAG-3$^+$ cells in PBMCs x mean of fluorescence intensity of the LAG-3$^+$ cells, plotted as a function of antibody concentration.

FIG. 7: Complement-Dependent Cytotoxicity induced by A9H12 LAG-3 mAb.

A) hLAG-3-transfected and wild type CHO cells were labelled with FITC-conjugated anti-LAG-3 mAb (17B4) and the expression of LAG-3 on cell surface was analysed by flow cytometry using a FACSCanto. The histogram plots represent the mean fluorescence intensity of wt CHO (gray) and LAG-3$^+$ CHO (dark).

B) hLAG-3-transfected and wt CHO cells were washed in complete medium (MEM supplemented with 10% heat inactivated Foetal Calf Serum, FCS) and incubated with 0.1 µg/ml of A9H12 LAG-3 mAb or mIgG2a isotype-control mAb (Southern Biotechnologies) in complete medium for 30 min at 4° C. Cells were then washed and incubated in complete medium (−Complement) or in MEM supplemented with 100 of freshly resuspended rabbit serum (Cerdalane Inc.) (+Complement) for 1 hour at 37° C. After washing, cells were stained with 7-AAD (Coulter Inc.) for 15 minutes at room temperature and immediately analysed by flow cytometry to determined the percentage of 7-AAD-positive cells corresponding to dead cells. Data represent the percentage of dead cells in each condition on hLAG-3-transfected and wt CHO cells as indicated.

C) LAG-3$^+$ CHO cells were incubated with indicated concentrations of A9H12 LAG-3 mAb for 30 min at 4° C. and then incubated with MEM supplemented with 25% rabbit serum for 1 hour at 37° C. After washing, cells were stained with 7-AAD (Coulter Inc.) and analysed by flow cytometry. The percentage of specific cytotoxicity is calculated according to the following formula $$\frac{(\text{Sample Death} - \text{Spontaneous Death}) \times 100}{(\text{Maximal Death} - \text{Spontaneous Death})}$$

where Sample Death is the percentage of 7-AAD-positive cells in each condition, Spontaneous Death, the percentage of 7-AAD-positive cells without mAb and Maximal Death, the percentage of 7-AAD-positive cells with 10 µg/ml mAb.

D) LAG-3$^+$ CHO cells were incubated with 0.1 µg/ml A9H12, 17B4 or 31G11 LAG-3 mAb or with their corresponding isotype controls (IgG2a, IgG1 or IgM, respectively) for 30 min at 4° C. and then incubated with MEM supplemented with 25% rabbit serum for 1 hour at 37° C. Specific cytotoxicity was determined as above with a Maximal Death corresponding to 10 µg/ml A9H12 (left panel) and 0.1 µg/ml A9H12 (right panel).

E) PBMCs were stimulated with SEB (1 µg/ml) to induce LAG-3 expression on T cells and then used as target cells in the CDC assay in the presence of A9H12 or 31G11 LAG-3 mAb or their isotype controls. After staining cells with fluorochrome-conjugated CD3, CD4, CD8, CD25 and 17B4, the percentage of 7-AAD-positive cells was analysed on the indicated T cell subpopulations. Data represent the percentage of dead cells in each population (with spontaneous death in the absence of mAb being subtracted).

FIG. 8: Antibody-Dependent Cell-mediated Cytotoxicity induced by A9H12 LAG-3 mAb A) Effector cells (PBMCs) were stimulated with IL-2 (100 IU/ml, BD Biosciences) for 1 day. Target cells (hLAG-3-transfected CHO cells) were labelled with CFSE (a fluorescent vital dye) and incubated with 1 µg/ml A9H12, mIgG2a, 17B4 or mIgGl for 20 min at room temperature. Effector cells and target cells were then mixed at indicated E:T ratios (E:T, Effector:Target) and incubated for 16 hours at 37° C. Non-adherent and adherent cells were harvested using Versene reagent, stained with 7-AAD and immediately analysed by flow cytometry to determine the percentage of 7-AAD-positive cells in the CFSE-positive population. Data represent the percentage of dead cells, with the non-specific cell death in the presence of the isotype control being subtracted.

B) CFSE-labelled wild-type or LAG-3$^+$ CHO target cells were incubated with indicated concentrations of A9H12 or mIgG2a and IL-2-stimulated PBMCs were added at a 50:1 E:T ratio and incubated for 16 hours at 37° C. Cell death was analysed as above and data represent the percentage of dead cells in CFSE-positive cells in the presence of A9H12 or its isotype-matched IgG2a control mAb.

FIG. 9: Incidence of arthritis (percentage of mice that developed CIA)

Male DBA/1 mice (n=22) were injected i.d. with bovine type II collagen (200 µg) emulsified in CFA containing 250 lug *M. tuberculosis*.

FIG. 10: Construction of the chimeric IMP731 therapeutic antibody.

FIG. 11: Expression plasmids for the light (panel A) and heavy (panel B) IMP731 chains.

FIG. 12: Final bi-cistronic plasmid construction used for the stable transfection of CHO cells.

FIG. 13: IMP731 binding on LAG-3$^+$ CHO and activated human T cells.

A) hLAG-3-transfected CHO were dissociated from culture plastic using VERSENE™ buffer containing cation-chelating agent, incubated with indicated concentrations of IMP731 Ab or its isotype control hIgG1 (Chemicon) for 30 min at 4° C., washed and then incubated with a FITC-conjugated F(ab)'2 goat anti-human IgG1 secondary antibody (5 µg/ml, SBA) for 30 minutes at 4° C. After washing, cells were analysed by flow cytometry using a FACSCanto™ (BD Biosciences) and the means of fluorescence intensity were plotted as a function of antibody concentration.

B) PBMCs from a healthy volunteer were stimulated for 2 days with SEB (1 µg/ml, Sigma Aldrich) to induce the expression of LAG-3 on T cells. PBMCs were stained as above. Data represent a weighted percentage, calculated as the percentage of LAG-3$^+$ cells in PBMCs×mean of fluorescence intensity of the LAG-3$^+$ cells, plotted as a function of antibody concentration.

FIG. 14: Complement-Dependent Cytotoxicity induced by IMP731 LAG-3 mAb hLAG-3-transfected CHO cells were incubated with 1 µg/ml of IMP731 Ab or hIgGl isotype-control mAb (Chemicon) in complete medium (MEM supplemented with 10% heat inactivated Foetal Calf Serum, FCS) for 30 min at 4° C. Cells were then washed and incubated in complete medium (without Complement) or in MEM supplemented with 25% of freshly resuspended rabbit serum (Cerdalane Inc.) (with Complement) for 1 hour at 37° C. After washing, cells were stained with 7-AAD (BD Biosciences) for 15 minutes at room temperature and immediately analysed by flow cytometry to determine the percentage of 7-AAD-positive cells corresponding to dead cells. Data represent the percentage of dead cells in each condition as indicated.

FIG. 15: Antibody-Dependent Cell-mediated Cytotoxicity induced by IMP731.

A) Effector cells (PBMCs) were stimulated with IL-2 (100 IU/ml, BD Biosciences) for 1 day. Target cells (hLAG-3-transfected CHO cells) were labelled with CFSE (a fluorescent vital dye) and incubated with 1 µg/ml IMP731 or hIgGl for 10 min at room temperature. Effector cells and target cells were then mixed at indicated E:T ratios (E:T, Effector:Target) and incubated for 16 hours at 37° C. Cells were stained with 7-AAD and immediately analysed by flow cytometry to determine the percentage of 7-MD-positive cells in the CFSE-positive population. Data represent the percentage of dead cells.

B) CFSE-labelled LAG-3$^+$ CHO target cells were incubated with indicated concentrations of IMP731 or hIgGl and IL-2-stimulated PBMCs were added at a 50:1 E:T ratio and incubated for 16 hours at 37° C. Cell death was analysed as above in CFSE-positive population. The percentage of specific cytotoxicity, calculated according to the following formula $$\frac{(\text{Sample Death} - \text{Spontaneous Death}) \times 100}{(\text{Maximal Death} - \text{Spontaneous Death})}$$

where Sample Death is the percentage of 7-AAD-positive cells in each condition, Spontaneous Death, the percentage of 7-MD-positive cells without Ab and Maximal Death, the percentage of 7-MD-positive cells with 1 µg/ml IMP731

C) Effector cells (PBMCs) were stimulated with IL-2 (100 IU/ml, BD Biosciences) for 1 day. Target cells (hLAG-3$^+$ CHO cells or hLAG-3$^-$ CHO cells) were labelled with CFSE (a fluorescent vital dye) and incubated with 1 µg/ml IMP731 or hIgGl for 10 min at room temperature. Effector cells and target cells were then mixed at indicated E:T ratios (E:T, Effector:Target) and incubated for 16 hours at 37° C. Cells were stained with 7-AAD and immediately analysed by flow cytometry to determine the percentage of 7-AAD-positive cells in the CFSE-positive population. Data represent the percentage of dead cells.

FIG. 16 depicts ADCC activity of IMP731 using CMV peptides-activated human T cells. This ADCC assay was performed with PBMCs from a CMV-positive human donor stimulated with a CMV peptide pool. Various concentrations of IMP731 or human igG1 were added for 4 hr. Then, the cells were phenotyped to evaluate the percentage of activated T cells remaining. The dose-dependent decrease of the percentage of activated CD8$^+$ (panel A, left) or CD4$^+$ (panel A, right) T cells expressing LAG-3 induced by IMP731 versus its isotype-matched hIgG1 control) is presented. Panel B presents the percentage of CD3$^+$ CD8$^+$ and CD3$^+$ CD4$^+$ cells expressing CD25 and/or LAG-3 with 10-ng/ml of IMP731 or hIgG1.

Figure 19:
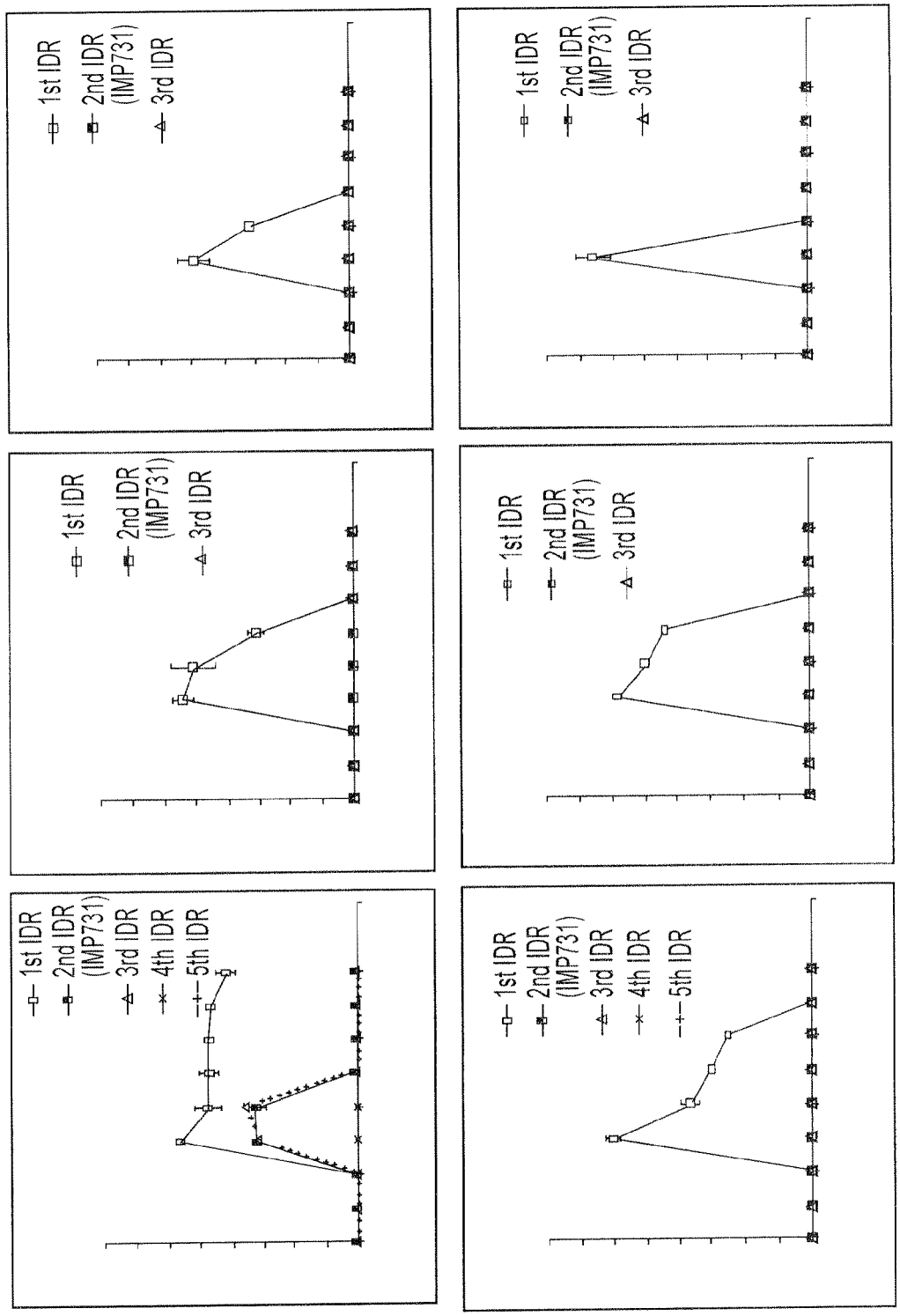

FIG. 19 depicts the size of the DTH reaction of three baboons to a full (1:1 dilution) or a suboptimal tuberculin dose (1/50 dilution). Open symbols show the first reference DTH, dark symbols the subsequent DTH performed after i.v. injection of 0.1 mg/kg of IMP731. IDR means intra-dermal reaction.

FIG. 20 are DNA and amino acid sequences for the light chain kappa region of IMP731, including the variable region sequences and the amino acid sequences for CDR-L1, -L2 and -L3. FIG. 20 discloses SEQ ID NOS 12-13, 8, 14 and 17-18, respectively, in order of appearance.

FIG. 21 are DNA and amino acid sequences for the heavy chain gamma region of IMP731, including the variable region sequences and the amino acid sequences for CDR-H1, -H2 and -H3. FIG. 21 discloses SEQ ID NOS 15, 16, 10, 11 and 19-21, respectively, in order of appearance.

Figure 22:
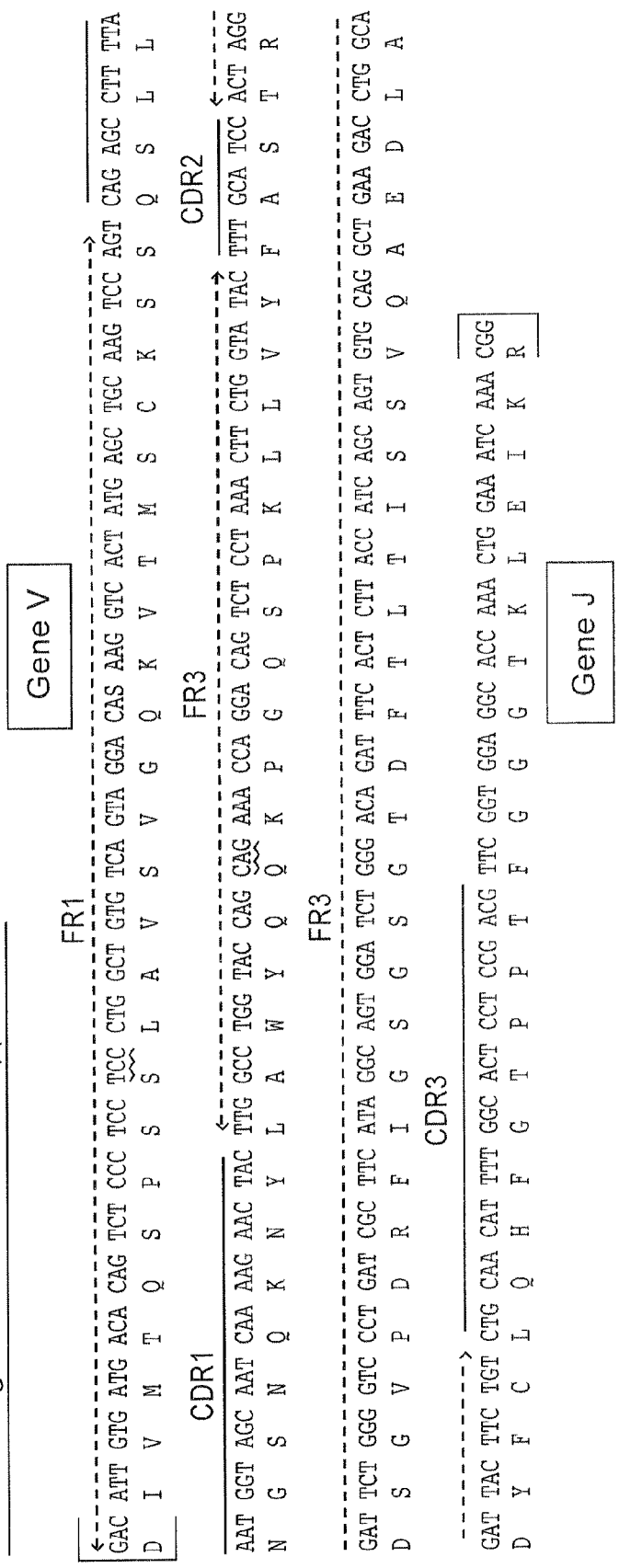

FIG. 22 shows the characterization of variable and signal peptide sequences of the kappa chain from IMP731 recombinant antibody. FR, Framework; CDR, Complementarity Determining Region. FIG. 22 discloses SEQ ID NOS 22-23, 8 and 14, respectively, in order of appearance.

Figure 23:
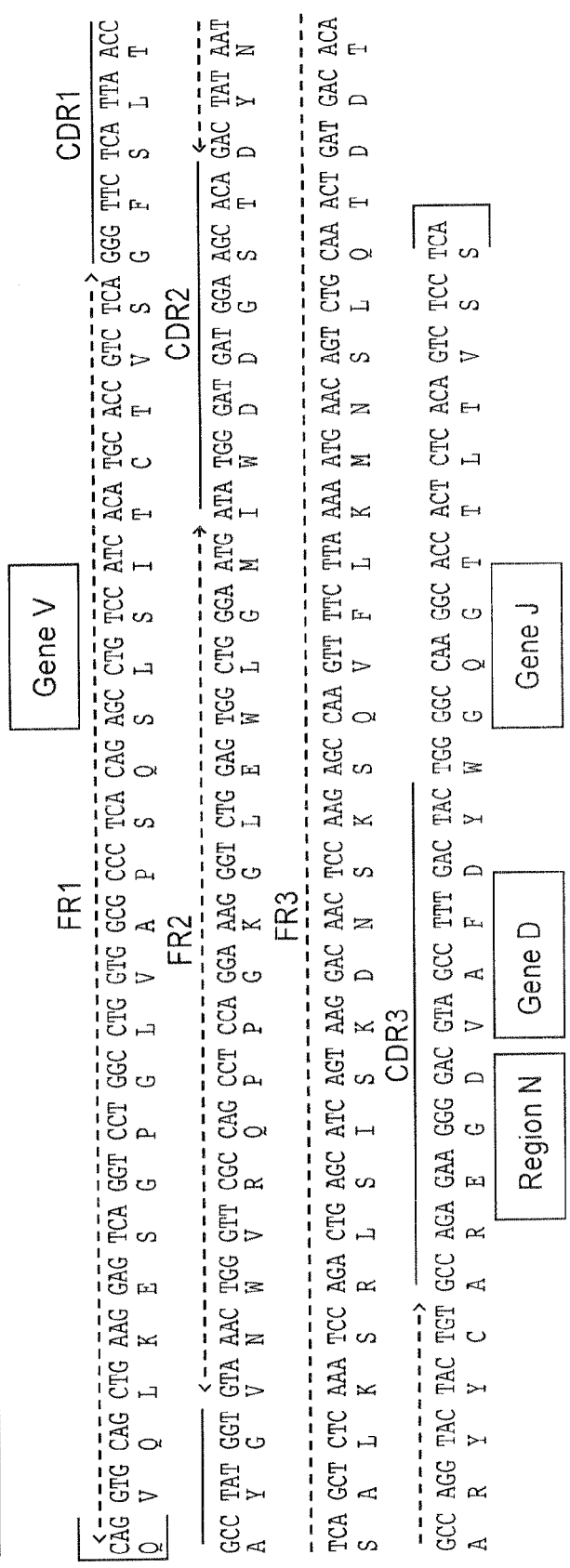

FIG. 23 shows the characterization of variable and signal peptide sequences of the gamma chain from the I MP731 recombinant antibody. FR, Framework; CDR, Complementarity Determining Region. FIG. 23 discloses SEQ ID NOS 24-25, 10 and 11, respectively, in order of appearance.

V. DETAILED DESCRIPTION

The present invention provides molecules binding to LAG-3 protein and causing depletion of LAG-3+ activated T cells. Said depletion can be measured by changes in peripheral blood lymphocyte numbers, a tissue or an organ.

The present invention relates preferably to human LAG-3 protein (hLAG-3 also named hereafter LAG-3). In a preferred embodiment the molecule binding to LAG-3 protein is a cytotoxic anti-LAG-3 monoclonal antibody or fragment thereof causing depletion of LAG-3+ activated T cells, said antibody comprising an Fc fragment from the human IgG1 or IgM (or mouse IgG2a) subclass and an Fab fragment which binds LAG-3 protein, said antibody exhibiting a complement-dependant cytotoxicity (CDC) and/or an antibody dependant-cell cytotoxicity activity (ADCC).

Lymphocyte activation gene-3 (LAG-3, CD223) is up-regulated during the early stages of T-cell activation. The present invention is based on the analysis of the effects of cytotoxic antibodies against LAG-3 in acute cardiac allograft rejection and in rheumatoid arthritis (in vivo animal studies) and in in vitro experiments where selected LAG-3 monoclonal antibodies are efficient at low doses (<0.1 µg/ml) at depleting LAG-3+ activated effector T cells.

Fully vascularized heterotopic allogeneic heart transplantation was performed in rats across a full-MHC mismatch barrier (LEW.1W into LEW.1A). Recipients received two injections (day 0 and 3) of antibodies directed to the extraloop domain of LAG-3 or control antibodies. Graft survival, histology, mRNA transcripts and alloreactivity of lymphocytes were tested.

It was first noted that LAG-3 mRNA molecules accumulate in cardiac allografts undergoing rejection, but not in peripheral lymphoid organs. Administration of anti-LAG-3 antibodies inhibited graft infiltration by effectors mononuclear cells and prolonged allograft survival from 6 days in control antibodies-treated recipients to a median of 27 days.

It was found that cells expressing LAG-3 infiltrate rejected heart allografts and that targeting LAG-3 using cytotoxic antibodies as induction monotherapy delays acute rejection by reducing graft infiltration by T cells and monocytes.

Experiments showing that short courses of CD40L antibody therapy could achieve long-term graft survival in mice and primates have been initially interpreted as an effect of costimulation blockade. However, Monk et al. (2) showed that much of the efficacy of anti-CD40L therapy derives not from costimulation blockade, but from destruction of activated T cells. The outcome is a selective purging of potentially aggressive T cells that have experienced antigen.

Collagen-induced arthritis (CIA) is a well-described animal model for rheumatoid arthritis. Collagen-induced arthritis is an autoimmune disease inducible in rats, mice and primates by immunization with heterologous type II collagen. The resulting joint pathology resembles rheumatoid arthritis with synovial proliferation, cell infiltration, cartilage erosion and bone resorption in the most severe cases (12).

Using particular immunization protocols, early studies have established a hierarchy of responsiveness to CIA linked to the H-2 haplotype, with H-$2^q$ (e.g. DBA/1 mice) being the most and H-$2^b$ (e.g.C57BL/6 mice) amongst the least responsive strains. However, some studies have shown that responsiveness to CIA may be less restricted by the MHC class II than previously thought and may be just as dependent on immunization conditions (13). The variety of type II collagen (CII) from different species and the preparation of complete Freund's adjuvant (CFA) with different concentrations of *Mycobacterium tuberculosis* were important parameters for arthritis development. Inglis et al. have shown that chicken, but not bovine, CII was capable of inducing disease in C57BL/6 mice, with an incidence of 50% to 75%. This is in contrast to DBA/1 mice, in which bovine, mouse and chicken CII all induced disease, with an incidence of 80% to 100%. The phenotype of arthritis was milder in C57BL/6 mice than in DBA/1 mice, with less swelling and a more gradual increase in clinical score (14). Moreover, male mice are frequently preferred for CIA studies, as the incidence of arthritis is somewhat higher in male than in female mice.

In mice, CIA is induced by an i.d. injection of type II collagen (CII) in the presence of CFA, usually followed by an i.p. boost injection of CII, without adjuvant, 21 days later. However, there are reported variations for almost every aspect of the immunization procedure and even in the highly susceptible DBA/1 strain the time of onset, severity and incidence of CIA can be variable (13, 15).

Therapeutic antibodies for the treatment of auto-immune diseases have already been described, like the TNFa mAbs in rheumatoid arthritis. By definition, LAG-3 (Lymphocyte Activation Gene-3) is a marker for recently activated effector T cells. Depleting these effector LAG-3+ T cells will lead to targeted immunosuppression (i.e. only activated T cells are suppressed, not all T cells as with corticoids or cyclosporin). This very specific immunosuppression should lead to higher therapeutic indices compared to classical immunosuppressive agents or to therapeutic antibodies (e.g. HUMIRA™, REMICADE™) or soluble receptors (e.g. ENBREL™) blocking TNFa. Thus, LAG-3 is a promising target available for a therapeutic depleting mAb approach to eliminate autoreactive activated effector T cells.

Molecules that bind to LAG-3 protein and cause depletion of LAG-3+ activated T cells, according to the present invention, include antibodies (mono or polyclonal, preferably monoclonal) and fragment thereof, peptides and organic small molecules.

Cytotoxic anti-LAG-3 monoclonal antibody or fragment thereof according to the present invention causes depletion of more than 30% preferably more than 50% of LAG-3+ activated T cells.

Cytotoxic anti-LAG-3 monoclonal antibody or fragment thereof according to the invention comprises antibodies with a murine IgG2a or a human IgG1 Fc region giving strong CDC or ADCC properties.

Cytotoxic anti-LAG-3 monoclonal antibody or fragment thereof according to the present invention exhibits (i) more than 50% of maximal CDC activity at a mAb concentration of less than 0.1 µg/ml and/or (ii) more than 50% of maximal ADCC activity at a mAb concentration of less than 0.1 µg/ml.

Cytotoxic anti-LAG-3 monoclonal antibody or fragment thereof, which suppresses a DTH reaction in a mammal after a single dose of 0.1 mg/kg.

Molecules binding to LAG-3 protein and more particularly cytotoxic anti-LAG-3 monoclonal antibody, causing depletion of LAG-3+ activated T cells and antibody, can be produced by methods well known to those skilled in the art.

Antibodies generated against CD223 polypeptides can be obtained by administering, in particular by direct injection, CD223 polypeptides to an animal, preferably a non-human. The antibody so obtained will then bind the CD223 polypeptides itself. In this manner, even a sequence encoding only a fragment of the CD223 polypeptide can be used to generate antibodies binding the whole native CD223 polypeptide.

For preparation of monoclonal antibodies, any technique which provides antibodies produced by continuous cell line cultures can be used. Examples include the hybridoma technique (9), the trioma technique, the human B-cell hybridoma technique (10).

Techniques described for the production of single chain antibodies (U.S. Pat. No. 4,946,778) can be readily used to produce single chain antibodies to CD223 polypeptides. Also, transgenic mice may be used to express humanized antibodies to immunogenic CD223 polypeptides.

An antibody of the present invention includes intact antibodies, an antibody fragment, a humanized antibody, a conjugate, a fusion protein or a bi-specific antibody that contains a $V_H$-$V_L$ pair where the CDRs form the antigen binding site. The invention also includes antibodies in which the Complementarity Determining Regions (CDRs) of one of the antibodies of the invention, such as those set forth in FIGS. 22 and 23, are transferred from the native framework (FR) to a different FR. The antibody of the invention could be produced recombinantly, according to methods known in the art.

For instance, a first monoclonal antibody according to the present invention, called A9H12, is produced by the hybridoma deposited at the CNCM on Apr. 27, 2007 under the access number CNCM I-3755.

A second monoclonal antibody according to the present invention, called 31G11, is produced by the hybridoma deposited at the CNCM on Apr. 27, 2007 under the access number CNCM I-3756.

A third monoclonal antibody according to the present invention, called IMP731, is produced by chimerization of monoclonal antibody A9H12 with human IgG1 Fc region, as described and characterized in Examples 4, 5 and 6.

The antibodies of the present invention include those that have the same CDRs as the above antibodies (A9H12, 31G11 or IMP731) but have differences due to glycosylation patterns or post translational modifications.

The invention is also directed to the use of a cytotoxic anti-LAG-3 monoclonal antibody or fragment thereof for the manufacture of a medicament for treating or preventing organ transplant rejection or for treating autoimmune disease.

Biologically active fragments of the monoclonal antibodies of the present invention exhibit some or all of the biological activities of the monoclonal antibody. For example, biologically active fragments of IMP731 exhibit the same high binding affinity as IMP731, as assessed in a standard assay such as a Biacore analysis. Biological activity may also be assessed by other in vitro or in vivo assays, which are known to the skilled artisan and which are used to assess and characterize the monoclonal antibodies of the invention. One such assay assesses DTH reaction in baboons. Another in vitro assay is the ADCC bioassay described in Example 5 and FIG. 16 and related description. In one embodiment, the invention relates to the ADCC assay described in Example 5 and in FIG. 16 and to the use of such assay in identifying depleting LAG-3 antibodies or fragments thereof that have an EC50 of less than 5 ng/ml.

The present invention also relates to an antibody other than IMP731 which comprises the kappa or gamma regions of IMP731 and which has the same biological activity as IMP731. In another embodiment, the invention relates to antibodies or fragments thereof that compete with IMP731 in binding LAG-3 protein and in causing depletion of LAG-3$^+$ activated T cells.

The nucleic acid sequences encoding the kappa and gamma regions of IMP 731 are set forth in FIGS. 20 and 21, respectively. The present invention includes these nucleic acid sequences and biologically active fragments and mutations thereof and nucleic acid molecules comprising these nucleic acid sequences, vectors comprising these nucleic acid molecules, cells comprising such vectors and pharmaceuticals comprising the nucleic acid molecules of the invention. The present invention also is directed to the polypeptides encoded by the nucleic acid molecules of the invention and particularly to polypeptides represented by the amino acid sequences set forth in FIGS. 20 and 21, and also polypeptides comprising such amino acid sequences and biologically active fragments and mutations of such amino acid sequences. In one embodiment, the invention is directed to molecules comprising the CDRs set forth in FIGS. 20 and 21 and further characterized in FIGS. 22 and 23 and to molecules comprising such CDRs that may have minor amino acid differences from the native sequences, wherein such molecules have an EC50 of less than 5 ng/ml in the ADCC bioassay using CMV-stimulated human CD4 and CD8 T cells.

The present invention further provides a method for treating or preventing organ transplant rejection or for treating autoimmune disease. Said method comprises the administration to a mammalian subject a therapeutically effective amount of a cytotoxic anti-LAG-3 monoclonal antibody or fragment thereof.

Organ transplant rejection refers to the graft of an organ in an allogenic host. It may be useful for treating organisms suffering from conditions resulting in an abnormally high T-cell population or deleterious T-cell activity, for example graft rejection mediated by host T-cells, graft vs. host disease and T-cell mediated autoimmune and inflammatory diseases such as rheumatoid arthritis, type 1 diabetes, muscular sclerosis, etc. The methods of the invention may be applied to any organism which contains T-cells that express CD223. This includes, but is not limited to, any mammal and particularly includes humans and mice.

Auto-immune diseases are diseases in which the subject's own immune system reacts against the subject cells. Autoimmune disease which are amenable to treatments according to the present invention include autoimmune hemolytic anemia, autoimmune thrombocytopenia purpura, Goodpasture's syndrome, pemphigus vulgaris, acute rheumatic fever, mixed essential cryoglobulinemia, systemic lupus erythematosus, insulin-dependent diabetes mellitus, rheumatoid arthritis, Grave's disease, Hashimoto's thyroiditis, myasthenia gravis, psoriasis and multiple sclerosis.

A method for depleting LAG-3$^+$ activated T cells from a sample from a patient according to the present invention comprises reacting the sample with an antibody composition comprising an antibody described above.

A pharmaceutical composition according to the present invention comprises from 0.1 to 300 mg per dose, preferably from 0.5 to 30 mg per dose, and more preferably from 5 to 10 mg per dose, of a cytotoxic monoclonal antibody described above and one or more pharmaceutically acceptable carriers, adjuvants and/or diluents for administration to a mammal. In another embodiment, the pharmaceutical composition according to the invention comprises from 0.01 to 30 mg per kg, preferably from 0.1 to 3 mg per kg, and more preferably from 0.5 to 1 mg per kg of the cytotoxic monoclonal antibody described above. One of skill in the art would understand that the pharmaceutical compositions of the invention could be adjusted to contain amounts of the cytotoxic monoclonal antibody that would vary depending upon the health, age, weight, and condition of the subject being treated.

The pharmaceutical compositions of the present invention may be specially formulated for administration in solid or liquid form according to methods well known to the skilled artisan. Suitable carriers, for instance, vehicles, adjuvants, excipients and diluents are well known to the skilled artisan. Suitable formulations include formulations for oral, aerosol, parenteral, subcutaneous, transdermal, transmucosal, intestinal, intramedullary, intravenous, intranasal, intraocular, intravenous and interperitoneal administration or injection are exemplary and are not intended to be limiting. Techniques for formulating the pharmaceuticals of the present invention may be found in *Remington's Pharmaceutical Sciences* 18$^{th}$ ed. Mack Publishing Co., Easton, Pa. (1990).

The pharmaceutical compositions of the invention may contain the cytotoxic monoclonal antibody of the invention in combination with one or more other therapeutic agents.

The following examples further illustrate the invention but should not be construed as limiting the scope of the invention.

EXAMPLE 1

LAG-3-Positive Cells Targeted with Cytotoxic Antibodies

Material and Methods
Animals and Transplantations

Eight- to 12-week-old male Lewis. IW (LEW. 1W, haplotype RT$^a$) and Lewis. IA (LEW. 1A, haplotype RT1$^a$) congeneic rats (Centre d'Elevage Janvier, Le Genest-Saint-Isle, France), differed in their entire MHC region. Heterotopic LEW.IW heart transplantation was performed as previously described (11). Graft survival was evaluated by palpation through the abdominal wall.

Anti-LAG-3 Antibodies

A synthetic peptide corresponding to the extraloop domain of the rat LAG-3 protein (NCBI accession nb DQ438937; peptide DQPASIPALDLLQGMPSTRRHPPHR (SEQ ID NO: 1)) was linked to ovalbumin and used to immunise two rabbits. Pre-immune and immune sera, collected on day 63 after the 4th immunisation, were assayed by ELISA on immunogen and peptide and by flow cytometry on Con-A activated rat spleen cells. Pre-immune sera were negative in both assays. Pooled immune sera presented a titer (dilution for 50% signal) of 1/60000 by ELISA and of 1/1000 by FRCS, and presented a specificity for activated T cells.

Complement-Dependant Cytotoxicity Assay

Complement-mediated antibody-dependent cytotoxicity was tested using rabbit sera against Lewis 1A T cells in a $^{51}$Cr release assay. A total of 2×10$^6$ Lewis 1A T cells were labelled with 30 µCi of $^{51}$Cr for 90 min at 37° C. in RPMI (GIBCO) with 10% FCS. After three washes, T cells were distributed in 96 V-bottomed plates and incubated with rabbit complement and serial dilutions of heat-inactivated rabbit serum. After 4 h at 37° C., $^{51}$Cr release was measured in the supernatants using a scintillation counter. Specific cytotoxicity was calculated according to the following formula: (experimental release–spontaneous release)×100/(maximum release–spontaneous release).

In Vivo Antibody-Induced Cytotoxicity

Cytotoxic activity of anti-LAG-3 antibodies against LAG-3$^+$ cells was evaluated in vivo. ConA-activated (48 h) LEW.1W splenocytes were labelled with the CFSE and transferred (10$^8$ cells) into irradiated (4.5 Gy, day −3) LEW.IA recipients, together with anti-LAG-3 antibodies. On day 1, recipients were sacrificed and the presence of CFSE-positive cells evaluated by flow cytometry in lymphoid organs and in the blood.

Immunostaining

Graft samples were embedded in Tissue Tek (OCT Compound, Torrance, Calif., USA), snap-frozen in liquid nitrogen, cut into 5 µm sections and fixed in acetone. Endogenous biotin activity was blocked using the Dako biotin blocking system (Dako, Trappes, France). Sections were then labelled by a three-step indirect immunoperoxidase revelation. The area of each immunoperoxidase-labeled tissue section infiltrated by cells was determined by quantitative morphometric analysis. Positively stained cells on each slide were counted by morphometric analysis using point counting analysis (14) with a 121-intersection squared grid in the eyepiece of the microscope. Briefly, the percentage of the area of each graft section occupied by cells of a particular antigenic specificity (area infiltrate) was calculated as follows: [number of positive cells under grid intersection/(total number of grid intersections=121)]×100. The graft sections were examined at a magnification of ×400. The accuracy of the technique is proportional to the number of points counted. Thus, to maintain a SE of <100, 15 fields were counted for each labeled section. Results are expressed as the percentage of the area of the tissue section infiltrated by leukocytes (determined with OX1, OX30 labeling) and the phenotypic composition of the infiltrate and subpopulations which are related to the percentage of total leukocytes and are expressed as the percentage of leukocytes.

Graft Infiltrating Cell Extraction Staining

Dilacerated hearts were digested with collagenase D (2 mg/ml; Boehringer Mannheim) for 10 min at 37° C. Cells were then collected by extraction through a stainless steel mesh. The resulting suspension was then clarified by Ficoll isolation.

Quantitative RT-PCR

Real-time quantitative PCR was performed in an Applied Biosystems GENAMP™ 7700 Sequence Detection System using SYBR™ Green PCR Core Reagents (Applied Biosystems, Foster City, Calif.). The following oligonucleotides were used in this study: rat LAG-3: upper primer is 5'-ATAT-GAATTCACAGAGGAGATGAGGCAG-3' and lower primer is 5'-ATATGAATTCTCCTGGTCAGAGCTGCCT-3'. Rat INFg: upper primer is 5'-TGGATGCTATGGAAG-GAAAGA-3' and lower primer is 5'-GATTCTGGTGA-CAGCTGGTG-3'. Rat HPRT: upper primer is 51-CCTTGGTCAAGCAGTACAGCC-3' and lower primer is 5'-TTCGCTGATGACACAAACATGA-3'. A constant amount of cDNA corresponding to the reverse transcription of 100 µg of total RNA was amplified in 25 Ml of PCR mix containing 300 nM of each primer; 200 µM dATP, dGTP, dCTP; 400 µM dUTP; 3 mM MgCl$_2$; 0.25 U of uracyl-N-glycosylase; 0.625 U of AmpliTaq Gold DNA polymerase. The mix was subjected to 40 cycles of amplification. The real-time PCR data were plotted as the AR$_n$, fluorescence signal vs. the cycle number. The AR$_n$ values were calculated by the Applied Biosystems 7700 sequence detection software using the formula: $\Delta R_n = (R_n^+) - (R_n^-)$, where $R_n^+$ is the fluorescence signal of the product at any given time, $R_n^-$ is the mean fluorescence signal during cycles 3-13 and referred to as the baseline. The Ct value is defined as the cycle number at which the $\Delta R_n$ crosses a threshold. The threshold is set above the background fluorescence to intersect the exponential portion of the amplification curve of a positive reaction. The Ct is inversely proportional to the log amount of template within the PCR.

Statistical Analyses

Statistical significance was evaluated using as Mann-Whitney test for the comparison of two groups. Graft survival was evaluated by Kaplan-Meier analysis using the log rank test.

Results

Figure 1:
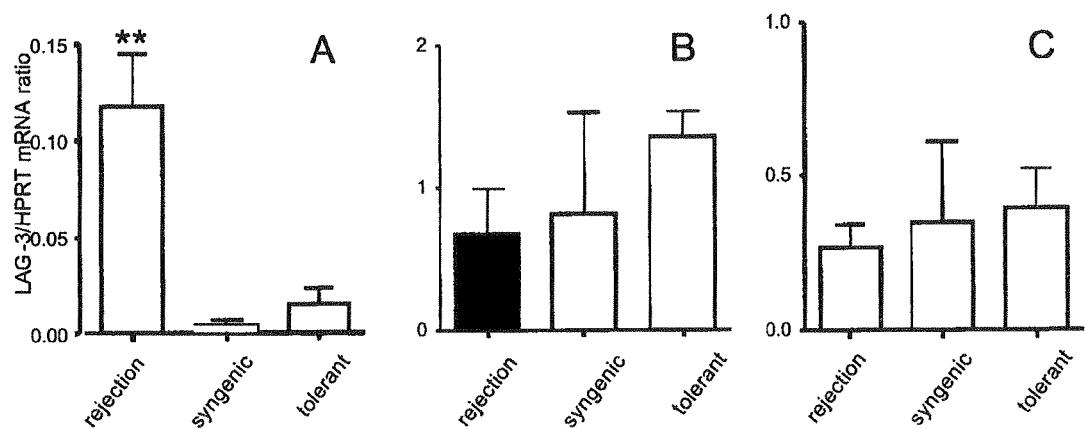

LAG-3 mRNA expression in rejected allograft and lymphoid organs LAG-3 is expressed by activated T cells in inflamed lymphoid organs and tissues (7). In order to see if LAG-3 is also expressed in rejected allografts, hearts grafts from LEW.1W to LEW.IA rat recipients were analyzed on day 5 (rejection occurring on day 6). Messenger RNA for LAG-3 was analyzed and compared with allografts receiving a tolerance-inducing regiment (anti-CD28 antibodies+CSA, as described (16)) and with isografts. Rejected allografts presented a 7-fold and a 25-fold accumulation of LAG-3 mRNA as compared with tolerated and syngeneic grafts, respectively (FIG. 1A). Such an accumulation was not detected in lymph nodes (FIG. 1B) or in the spleen of rejecting recipients (FIG. 1C).

Mechanism of Action of Anti-LAG-3 Antibodies

Figure 2:
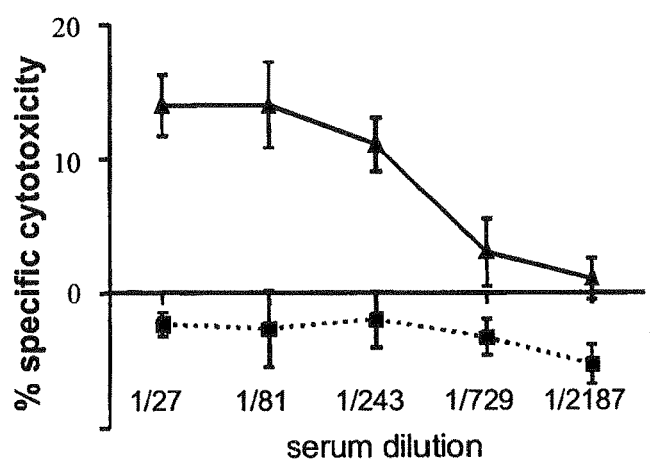

Anti-LAG-3 antibodies were produced in rabbits by immunization with a synthetic peptide from the extra-loop of LAG-3 Ig-like N-terminal domain, involved in the interaction of LAG-3 with Class II (ref PNAS Huard 1997). Post-immune serum, as well as the IgG fraction, stained <1% of rat spleen cells and 400 of rat spleen cells activated for 48 h with ConA, PMA+ionomycin or PHA. Pre-immune serum was negative (data not shown). In order to characterize the effect of anti-LAG-3 antibodies on LAG-3$^+$ cells, complement and ADCC-dependant cytotoxicity was assayed in vitro. Fifteen % of ConA-activated spleen cells were lysed in the complement-dependant cytotoxicity assay (FIG. 2). Given that only 400 of the ConA-activated target cells expressed LAG-3, this assay revealed that about 37 a of the LAG-3$^+$ spleen cells present in the preparation were lysed in vitro as a result of complement activation.

Figure 3:
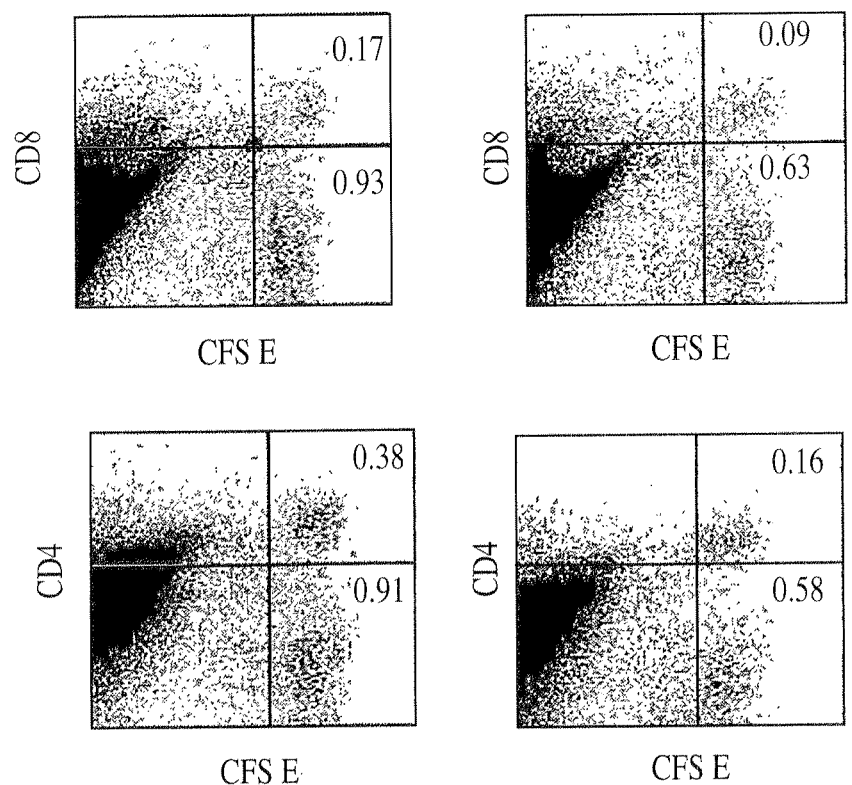

In vivo, the depleting activity of anti-LAG-3 antibodies was estimated by measuring the fate of CFSE-labeled activated T cells adoptively transferred to irradiated rat recipients. One day after the injection of therapeutic doses of anti-LAG-3 immune serum, only half the amount of CFSE$^+$/CD4$^+$ and CFSE$^+$/CD8$^+$ cells could be recovered from the spleen, as compared with similar injections of pre-immune serum (FIG. 3).

Anti-LAG-3 Antibodies Delay Heart Allograft Rejection

Figure 4:
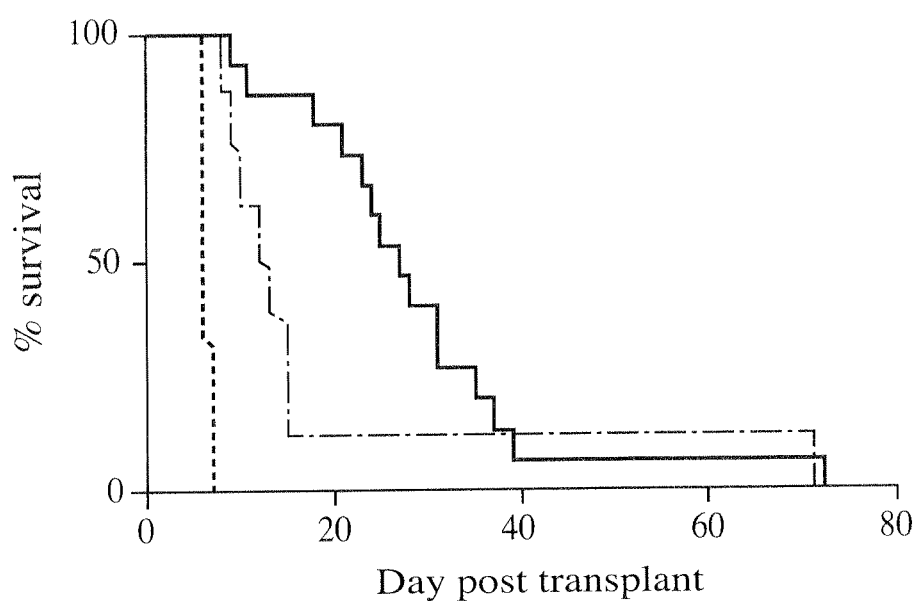
Figure 5:
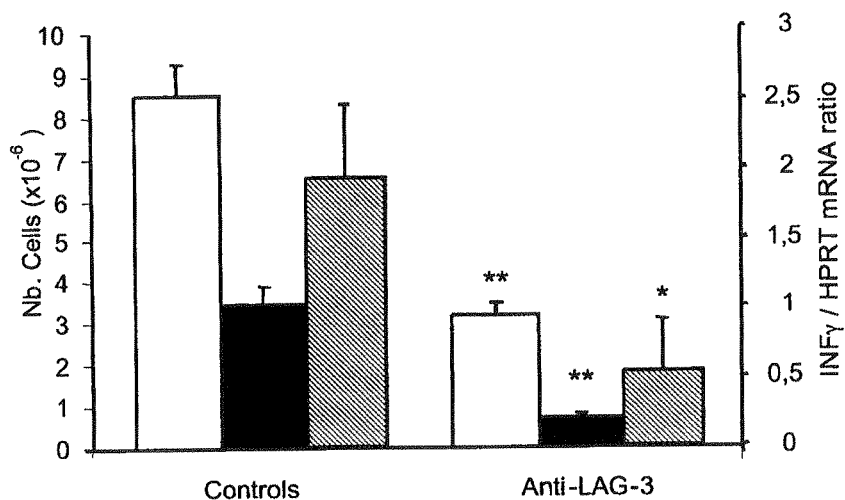

From preliminary pharmacokinetic observations, we established that two i.v. injections of 600 μl of anti-LAG-3 rabbit serum on days 0 and 3 resulted in the maintenance of anti-LAG-3 binding activity in recipient's serum for at least 2 weeks. This treatment delayed cardiac allograft rejection from 6 days in untreated and control-treated recipients to a median of 27 days. All recipients, however, eventually rejected their graft within 10 weeks (FIG. 4). On day 5, grafts from control-treated recipients were heavily infiltrated by activated T cells and this infiltrate was less important in anti-LAG-3 treated recipients. Infiltration by CD25$^+$ cells and NK cells, however, was not modified by the treatment. Since our anti-LAG-3 antibodies do not recognize LAG-3 in immunohistology, LAG-3 expression by graft infiltrating cells (GICs) was analyzed by flow cytometry after extraction. An average of 8.5 10$^6$±0.76 GICs could be recovered from control rejected grafts. From heart allografts from anti-LAG-3 treated recipients, only 3.16±0.44 10$^6$ GICs could be recovered (n=3; p<0.005). GICs contained 41.17±1% LAG-3$^+$ cells in controls (i.e. 3.5 10$^6$ cells) versus 22.2±0.9% in treated animals (i.e. 0.7 10$^6$ cells; n=3; p<0.0005; FIG. 5). Analysis of mRNA transcript reinforced these observations that infiltration of heart graft by mononuclear cells was reduced since we measured four times less INFγ mRNA molecules in treated grafts (FIG. 5).

Anti-LAG-3 Antibodies Inhibit Ongoing Acute Heart Allograft Delay Rejection

In order to investigate whether anti-LAG-3 antibodies might serve as a treatment of an ongoing acute allograft rejection, we grafted LEW.1W hearts into LEW.1A allogenic recipients that we maintained untreated over 3 or 4 days. At that time, recipients received an injection of 600 microliter of control or anti-LAG-3 rabbit serum. Control-treated recipients rejected the allografts on day 5 whereas anti-LAG-3 antibodies-treated recipients rejected only on day 11 (Table 1).

TABLE 1

Heart graft recipients were treated on day 3 or 4 with control or anti-LAG-3 antibodies. Rejection was monitored by daily heart palpation.

| Treatment | Day of rejection | Median survival |
| --- | --- | --- |
| Control serum on day 3 | 5, 5, 5 | 5 |
| Control serum on day 4 | 5, 5, 5 | 5 |
| Anti-LAG-3 serum on day 3 | 12, 13, 9 | 12 (p < 0.05 vs. control) |
| Anti-LAG-3 serum on day 4 | 10, 13, 13, 19 | 12.5 (p < 0.05 vs. control) |

EXAMPLE 2

Generation of New High Affinity hLAG-3 mAbs

Material and Methods

Mice were immunized 3 times with hLAG-3-transfected CHO cells (10$^7$ cells, intra-peritoneal injection), followed by a boost i.v. injection with 10 μg IMP321, the clinical-grade hLAG-31 g recombinant protein. Three days after the boost, splenocytes were fused with the X63.AG8653 fusion partner to yield hybridoma cells. Supernatants from hybridomas were screened for their specific binding (FACS analysis) on hLAG-3-transfected CHO versus wild type (wt) CHO cells.

One murine IgG2a antibody (580.1E MM H12, called A9H12) was selected, subcloned to yield a stable cell line and further characterized for its potency to deplete LAG-3$^+$ cells through CDC (complement-dependent cytotoxicity) and ADCC (antibody-dependent cell-mediated cytotoxicity), given that the murine IgG2a Pc region is known to be the most efficient Fc isotype in mice at delivering these activities, even on heterologous cells (i.e. CHO cells or human PBMCs). Similarly, a second IgM antibody (31G11E8, called 31G11) was also selected.

Results

Figure 6:
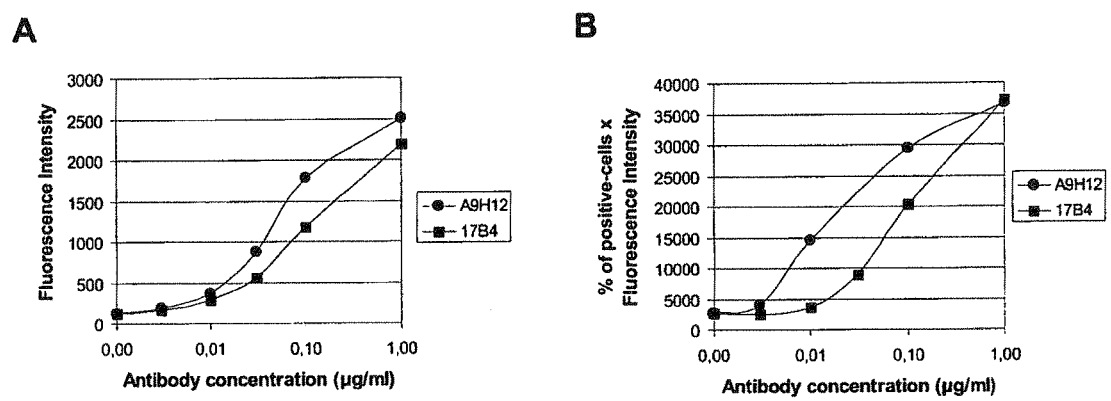

Dose-dependent binding of A9H12 was first compared to the reference LAG-3-specific 17B4 mAb on hLAG-3-transfected CHO cells and on LAG-3$^+$ in vitro activated human T cells (FIG. 6). A9H12 displayed a greater binding than the reference 17B4 mAb on both cell types. For instance, significant binding of A9H12 to activated human T cells was observed with a concentration as low as 0.01 µg/ml.

Figure 7:
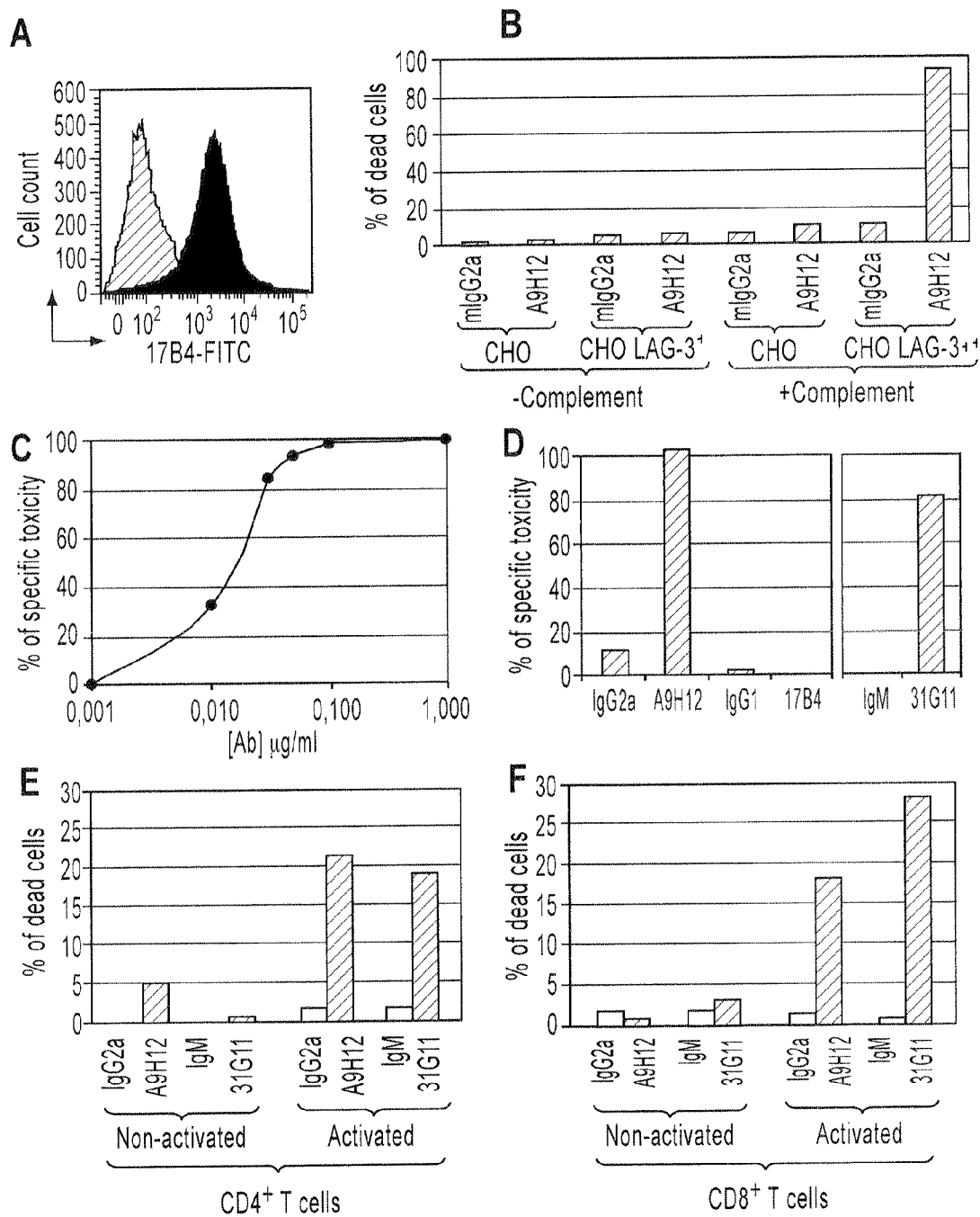

For CDC testing, the target cells used in this assay were LAG-3$^+$ CHO cells compared to wt CHO cells (FIG. 7A). Both types of cells were incubated for 1 hour at 37° C. with either A9H12, its murine isotype-matched IgG2a negative control mAb, 31G11, its murine isotype-matched IgM negative control or the reference 17B4 (IgG1) mAb and rabbit serum containing active complement. Cell viability was then assessed using 7-Amino-Actinomycin D (7-AAD), a fluorescent dye labelling cells which have lost their membranous integrity, a phenomenon which appeared rapidly after death. The percentage of 7-AAD-positive CHO cells (i.e. dead target cells) was determined by flow cytometry analysis. A9H12 displayed a potent and specific cytotoxic activity in this CDC assay, killing only LAG-3$^+$ CHO cells in the presence of complement (FIG. 7B). The anti-LAG-3 Ab was titered down to determined the efficacy of the antibody to activate CDC at low concentration of antibody. A9H12 efficiently induced LAG-3$^+$ CHO cells killing at a concentration as low as 0.01 µg/ml (FIG. 7C). The IgG1 17B4 antibody was also tested in this assay and had no effect (FIG. 7D, left panel), showing that not all LAG-3 mAbs could induce cytotoxicity in this bioassay. As observed with A9H12, the second 31G11 LAG-3-specific mAb also induced LAG-3$^+$ CHO cells killing (FIG. 7D, right panel).

The CDC bioassay was also performed on PBMCs stimulated with the superantigen SEB. The cytotoxicity of A9H12 and 31G11 were analysed on both activated (namely CD25$^+$/LAG-3$^+$ cells) and non-activated (namely CD25$^-$/LAG-3$^-$ cells) CD4$^+$ helper T and CD8+ cytotoxic T cells. Only activated CD4+ and CD8$^+$ T cells were specifically killed by A9H12 and 31G11 (FIG. 7E), showing that activated human T cells are susceptible to A9H12- or 31G11-specific killing in the presence of complement.

Figure 8:
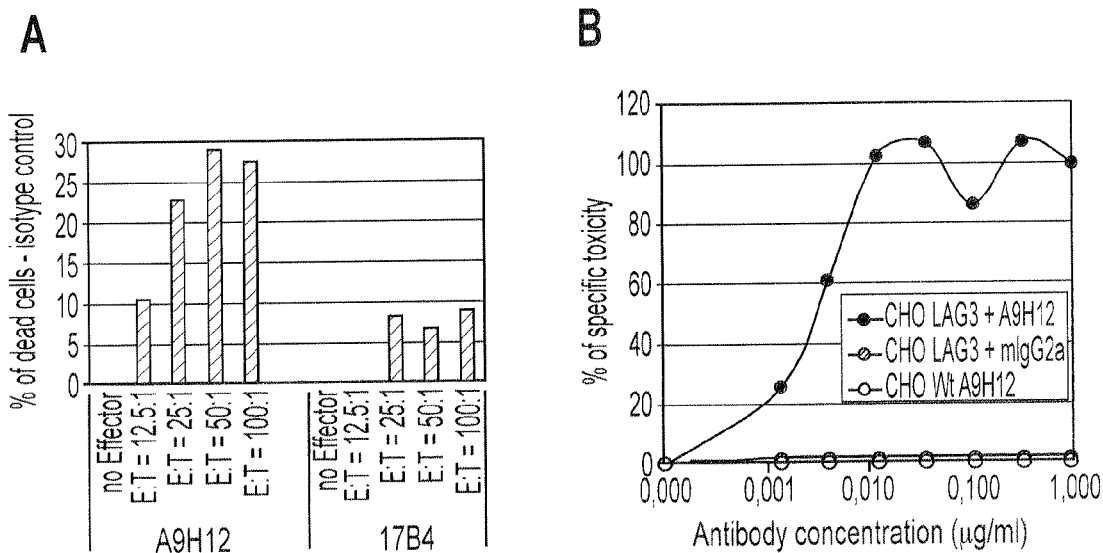

For ADCC testing, PMBCs were stimulated for one day with IL-2 to serve as effector cells and LAG-3$^+$ CHO cells were labelled with the vital dye CFSE to serve as target cells. In the presence of A9H12, PBMCs were able to kill a significant percentage of LAG-3$^+$ CHO cells and this effect was increased with the number of effector cells (FIG. 8A). In the presence of 17B4, only a small percentage of target cells was killed even at a high E:T ratio (FIG. 8A), showing that not all LAG-3 mAbs could induce cytotoxicity in this bioassay. The A9H12 LAG-3 mAb was titered down to determine the efficacy of the antibody to induce ADCC at low concentration of antibody. A9H12 efficiently induced LAG-3$^+$ CHO cells killing at a concentration as low as 0.01 µg/ml (FIG. 8B).

EXAMPLE 3

Testing Depleting LAG-3 Antibodies in a Collagen-Induced Arthritis Mouse Model

Material and Methods
Animals and Materials
Male DBA/1 (H-2$^q$) mice, 8-10 weeks old, were obtained from Janvier Laboratories. All animal experiments were performed according to local guidelines. BovineCII (joint cartilage) was purchased from BioCol. Incomplete Freund's adjuvant was provided by Sigma. Heat-killed *M. tuberculosis* H37Ra was purchased from Difco Laboratories.
Induction of Collagen-Induced Arthritis (CIA)
The induction and assessment of CIA were performed as previously described in two publications (13, 15). Complete freund's adjuvant was prepared by mixing 100 mg heat-killed *Mycobacterium tuberculosis* in 13. 3 ml IFA (final concentration 7.5 mg/ml). Bovine CII was dissolved at 3 mg/ml in 10 mm acetic acid overnight at 4° C. An emulsion was formed by mixing 2 volumes of CII with 1 volume of CFA. The CII solution and the emulsion with CFA were always freshly prepared. Male DBA/1 mice were intra-dermally injected at the base of the tail with a total of 100 µl of emulsion containing 200 µg CII and 250 µg *M. tuberculosis* on day 1 (D1). The injection was repeated at day 21 (D21). As control, three mice were injected with the emulsion of CFA without CII.

Clinical Assessment of Arthritis

Mice were examined for signs of arthritis three times a week from day 22. The disease severity was determined with the following scoring system for each limb: score 0= normal; score 1= swelling of footpad or joint; score 2= swelling of footpad and 1 or 2 joints; score 3= swelling of footpad and 3 or 4 joints; score 4=swelling of footpad and all joints. Each paw was graded, and the 4 scores were summed so that the maximum possible score was 16 per mouse. Incidence was expressed as the percentage of mice with an arthritis score≥1.

Results

Figure 9:
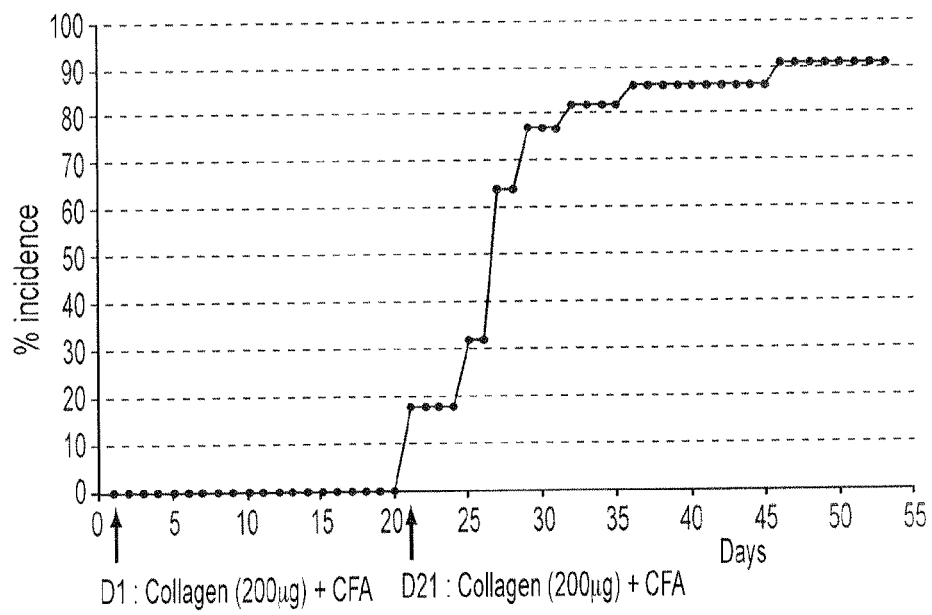

CIA was induced by i.d. injections of bovine type II collagen (CII) emulsified in CFA containing 250 µg *M. tuberculosis*. After one injection, 4 out of 22 mice had developed arthritis at D21. Two weeks after the second injection, at D35, 80-90% of the mice had developed clinical signs of arthritis (FIG. 9). The mice exhibited clinical scores covering the full range of responses from 1 to 16 with some limbs showing severe swelling of the footpad, ankle/wrist joint and digits (Table 2). None of the control animals (injected with CFA without CII) developed signs of arthritis (data not shown).

TABLE 2

Mean clinical scores (±SEM) over 55 days. Male DBA/1 mice (n = 10) were injected i.d. with bovine type II collagen (200 mg) emulsified in CFA containing 250 mg *M. tuberculosis* at D1 and D21.

| Days | Mean | SEM |
| --- | --- | --- |
| 25 | 2.2 | 0.9 |
| 27 | 2.7 | 0.8 |
| 29 | 5.7 | 1.0 |
| 32 | 9.2 | 1.5 |
| 34 | 10.5 | 1.5 |
| 36 | 10.9 | 1.6 |
| 39 | 10.8 | 1.7 |
| 41 | 10.9 | 1.6 |
| 43 | 11.2 | 1.5 |
| 46 | 11.7 | 1.3 |
| 53 | 13.1 | 1.2 |
| 55 | 13.3 | 1.1 |

Our results show that with the CIA protocol used, it is possible to obtain a high percentage (80-90%) of mice developing signs of arthritis. This experimental protocol provides a model to evaluate the therapeutic effect of depleting LAG-3 antibodies (specific for mouse LAG-3) in auto-immune diseases.

200 µg of the depleting LAG-3 mAb (A9H12 or 31G11) are injected i.p. or i.v. on day 15 and 25. Both a significant decrease in arthritis incidence and a significant lowering of mean clinical scores are involved.

EXAMPLE 4

Complement-Dependent Cytotoxicity (CDC) and Antibody-Dependent Cell-Mediated Cytotoxicity (ADCC) Induced by IMP731

Materials and Methods

A new murine mAb with depleting properties, A9H12, has been shown to recognize also baboon and macaque monkey LAG-3+ cells with high avidity and had been chosen as our lead depleting therapeutic mAb (ImmuTune IMP731).

A9H12 has been chimerized with a human IgG1 Fc region using standard genetic engineering and PCR protocols, to give CDC (complement-dependent cytotoxicity) and ADCC (antibody dependent cell cytotoxicity) properties.

Figure 10:
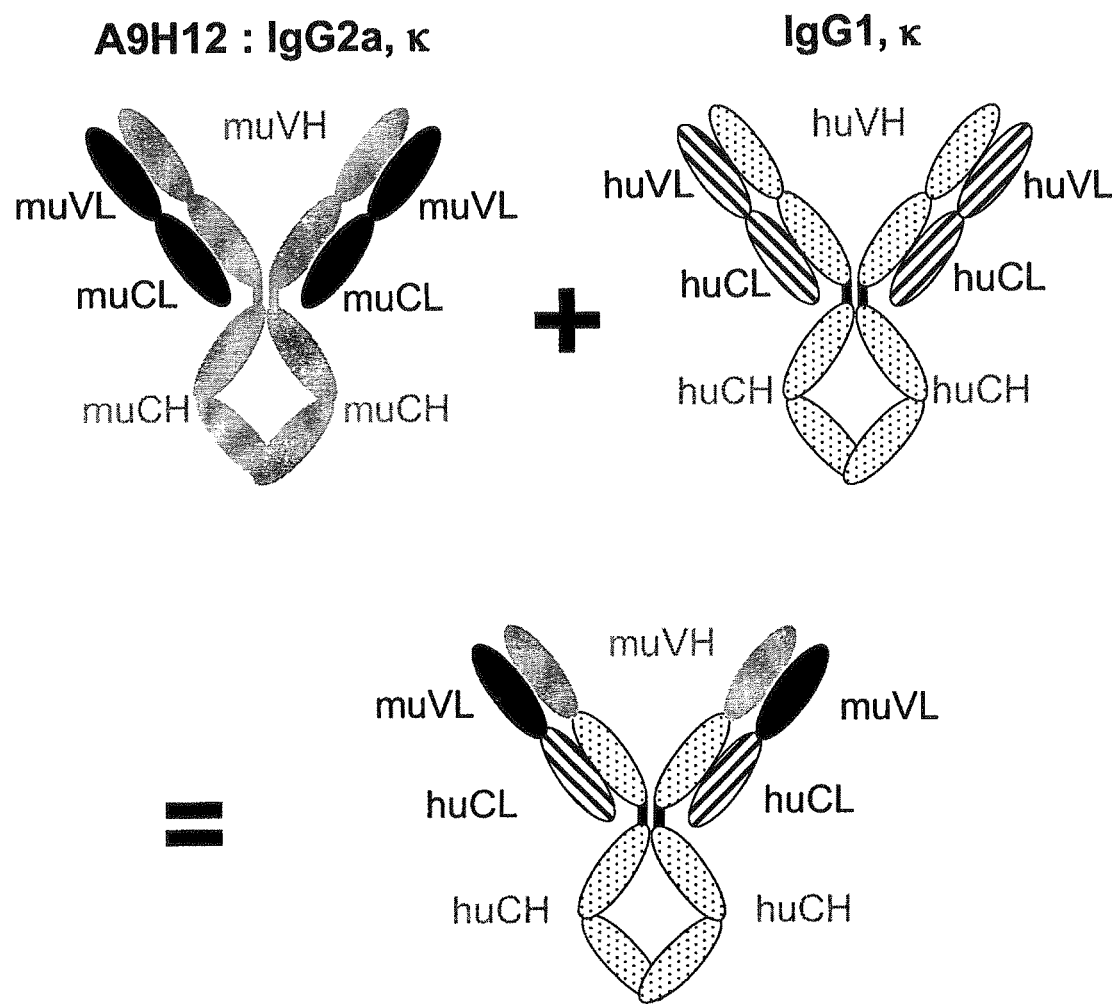

The A9H12 VH and VL cDNA sequences derived from A9H12 hybridoma cell mRNA were fused upstream of the human CH1-hinge-CH2-CH3IgG1 domains and Ckappa chains, respectively (FIG. 10).

The two light and heavy IMP731 chimeric chains were independently cloned into separate expression plasmids (FIG. 11 panel A and B, respectively) under the control of the PGK (or SRalpha in another construction, not shown) promoter. These 2 plasmids were cotransfected (transitory transfection) together into CHO cells and IMP731 was purified from the culture supernatant at day 2 or 3 by using protein A column affinity capture and elution at pH 3. After neutralisation with Tris-HCl the purified IMP731 antibody was tested in CDC and ADCC experiments for its ability to kill LAG-3+ target cells.

Figure 12:
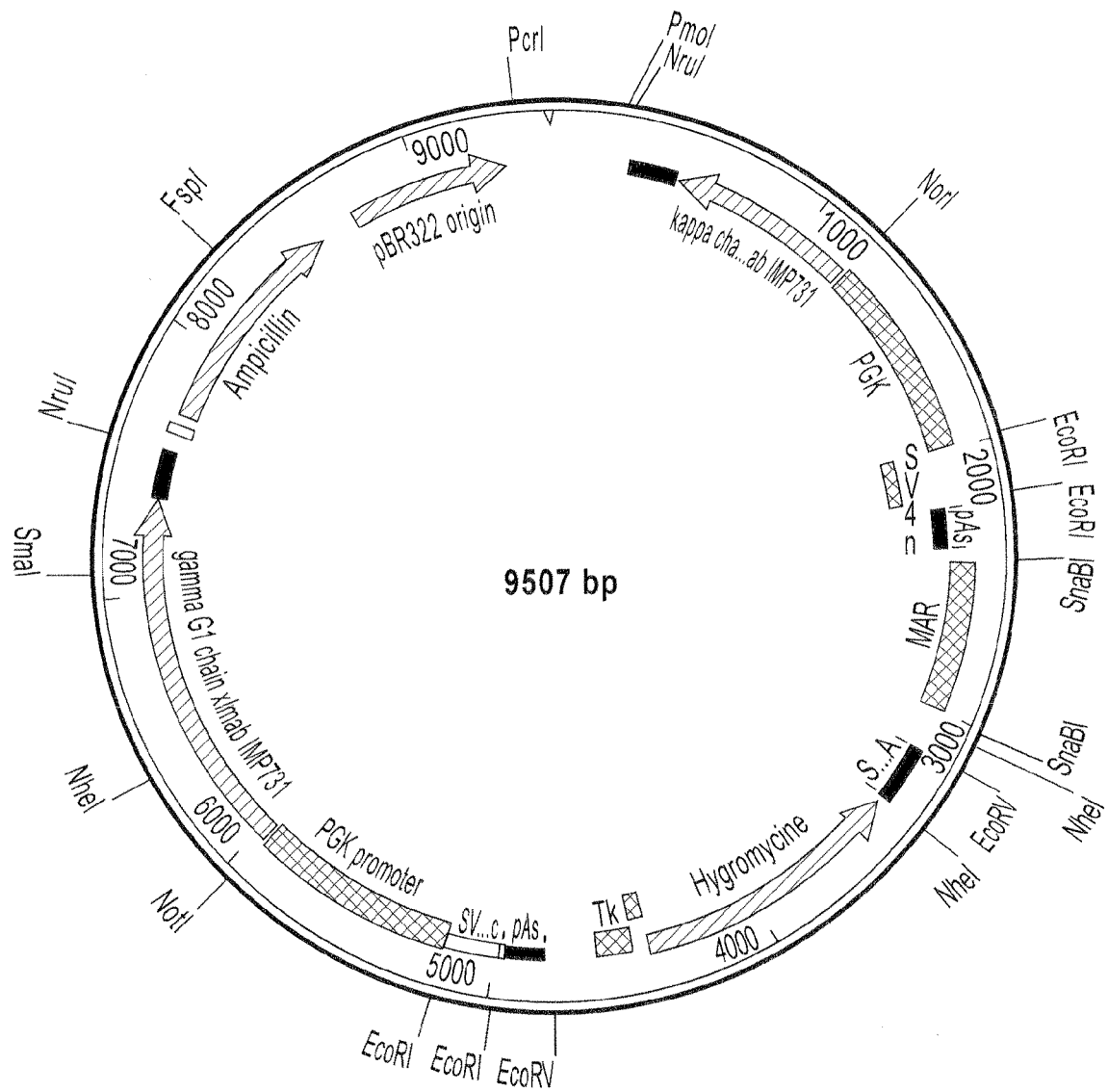

The two IMP731 light and heavy chains were then cloned together with the PGK (or SRalpha, not shown) promoter in a head-to-tail situation for coordinated expression of the two IMP731 chains from the same integration site (FIG. 12). This bi-cistronic IMP731 expression plasmid was used for stable transfection and selection of high-productivity (e.g. more than 20 picogramme IMP731 protein per million CHO-S cells per day) CHO-S cells using increasing concentrations of hygromycine in serum-free medium.

The DNA and protein sequences for the kappa region of IMP731 are set forth in FIG. 20 and the DNA and protein sequences for the gamma region of IMP731 are set forth in FIG. 21.

Results

Figure 13:
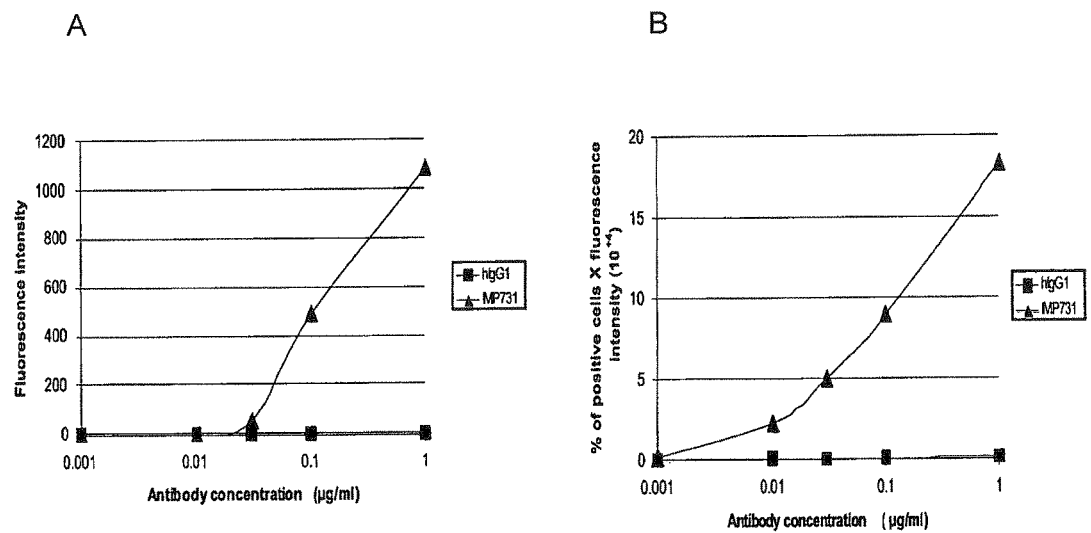

Dose-dependent binding of IMP731 was first assessed on hLAG-3-transfected CHO cells (FIG. 13A) and on LAG-3+ in vitro activated human T cells (FIG. 13B). IMP731 displayed a significant binding on both cell types with a concentration as low as 0.01 µg/ml for activated T cells.

Figure 14:
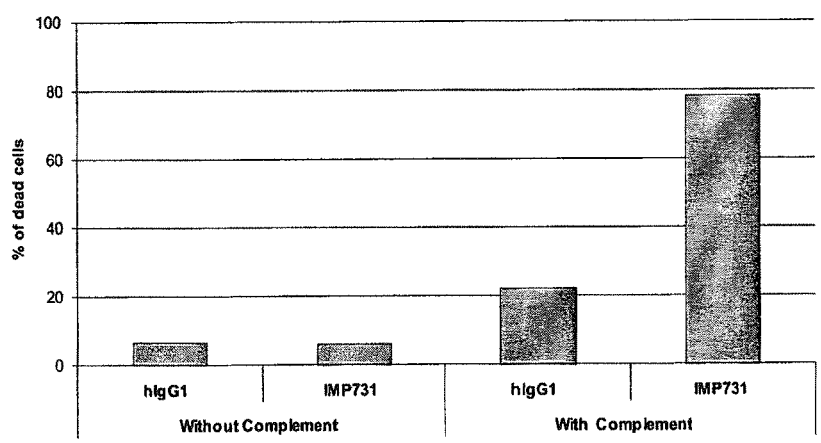

For complement dependent cytotoxicity (CDC) testing, the target cells used in this assay were LAG-3+ CHO cells (FIG. 14). Cells were incubated either with IMP731 or its human isotype-matched IgG1 negative control and then with rabbit serum containing active complement for 1 hour at 37° C. Cell viability was then assessed using 7-Amino-Actinomycin D (7-AAD). 7-AAD is a fluorescent dye labelling cells which have lost their membranous integrity, a phenomenon which appeared rapidly after death. The percentage of 7-AADpositive CHO cells (i.e. dead target cells) was determined by flow cytometry analysis. IMP731 displayed a potent and specific cytotoxic activity in this CDC assay, killing only LAG-3+ CHO cells in the presence of complement (FIG. 14).

For antibody-dependent cell-mediated cytotoxicity (ADCC) testing, PBMCs were stimulated for one day with IL-2 to serve as effector cells and LAG-3+ CHO cells were labelled with the vital dye CFSE to serve as target cells. In the presence of IMP731, PBMCs were able to kill a high percentage of LAG-3+ CHO cells (FIG. 15A). IMP731 LAG-3 Ab was titered down to determine the efficacy of the antibody in inducing ADCC at low concentration of antibody. IMP731 significantly induced LAG-3+ CHO cells killing at a concentration as low as 0.01 µg/ml (FIG. 15B). LAG-3+ but not LAG-3− cells were killed by the addition of IMP731 in this assay (FIG. 15C).

It appeared that binding and functional activities of IMP371 were similar to the parental A9H12 murine mAb produced by hybridoma cells. For instance, IMP731 has the same high affinity as the parent antibody, as assessed by BIACORE™ analysis.

| Antibodies: | ka (1/Ms) | kd (1/s) | KD (M) | Chi2 |
|---|---|---|---|---|
| A9H12 | $1.72 \times 10^6$ | $1.43 \times 10^{-3}$ | $8.29 \times 10^{-10}$ | 8.65 |
| IMP731 (chimeric A9H12) | $2.03 \times 10^6$ | $1.12 \times 10^{-3}$ | $5.51 \times 10^{-10}$ | 11.4 |

EXAMPLE 5

Antibody-Dependent Cellular Cytotoxicity (ADCC) of LAG-3+ Human T Cells Activated by a Recall Antigen Peptide Pool Using the IMP731 Therapeutic Antibody Introduction More than 80% of the population is cytomegalovirus (CMV) seropositive and more than 50% has a high frequency of circulating CMV-reactive T cells that can be analyzed in short-term in vitro assays in response to a CMV protein recall antigen. This is therefore a convenient setting in which to analyze IMP731-dependent antibody-dependent cellular cytotoxicity (ADCC) on subsets of antigen-specific T cells physiologically activated through peptide-dependent T-cell receptor triggering, using defined synthetic peptides (i.e. no antigenic contaminants) from the sequence of a CMV protein.

In addition, this experimental setting mimics closely the situation encountered in auto-immune diseases where circulating antigen-specific T cells are periodically stimulated by auto-immune recall antigens. For example in the case of psoriasis, the recall antigens are skin antigens that are presented to the immune system in the form of MHC-class I- and class II-restricted peptides.

Purpose

To assess the potency of IMP731 in killing activated antigen-specific human T cells stimulated with a CMV peptide pool and thus to estimate the lowest dose likely to have a pharmacological effect in man.

Experimental Design

PBMCs from CMV-positive donors were thawed, washed in complete RPMI 1640 supplemented with 10% FCS and seeded at $10^6$/ml in 24-well plate (1.75 ml/well) in the presence of a CMV peptide pool (BD Biosciences). The CMV peptide pool consists of a mix of 138 15-mers with 11 amino acid overlaps spanning the entire sequence of the pp65 protein (CMV AD169 strain). This peptide pool will induce MHC class II-restricted CD4 peptide-specific T cell activation and proliferation but will also activate MHC class I restricted CD8 peptide-specific T cells through the internalization and processing of 15-mers into 9-mers. Together the entire T cell repertoire specific for the pp65 protein will be activated. The final concentration of each peptide was 0.875 µg/ml. The cells were incubated at 37° C. for 5 days. As CD8

T cells proliferate more rapidly than CD4 T cells, there will always be more CD8 than CD4 activated T cells at day 5.

For ADCC testing, the cells were seeded in a 96-well U-bottom plate (180 μl/well, containing 150-175×10³ cells/well) in the CMV peptide-containing medium and 20 μl of 10× dilutions of IMP731 or its isotype-matched control (human IgG1, Chemicon) were added. After 4 hr at 37° C., the cells were stained with CD3-PE, CD4-PE-Cy7, CD8-APC-Cy7, CD25-APC (all from BD Biosciences) and FITC-conjugated anti-LAG-3 mAb (17B4 antibody, 1 μg/point) for 30 min at 4° C. After centrifuging, the cells were suspended for 15 min at room temperature in culture medium containing 2.5 μl 7-AAD (viability dye), before FACS analysis. After exclusion of dead cells based on size/granularity and 7-AAD staining, the percentages of LAG-3$^+$ and CD25$^+$ (another T cell activation marker) in the CD3$^+$ CD4$^+$ and the CD3$^+$ CD8$^+$ cells populations were analyzed.

Results

The stimulation of PBMCs with the CMV peptide pool induced the expression of the activation marker CD25 and LAG-3 (see FIG. 16) on a variable percentage of CD8$^+$ T cells (from 3 to 12% of T cells, 2 blood donors tested in different experiments) and CD4$^+$ T cells (lower percentages). In the presence of IMP731, the percentage of activated CD8$^+$ and CD4$^+$ T cells was dramatically reduced. A 70% reduction in the number of LAG-3$^+$ cells was observed both in the CD4 and the CD8 subsets at a 10 ng/ml IMP731 concentration (see FIG. 16, panel A). Similar results have been obtained at least twice in two donors. Additionally, the half maximal effective concentration (EC50) was found to be 1±0.4 ng/ml for CD4$^+$ T cells and 0.7±0.4 ng/ml for CD8$^+$ T cells (mean±sd of 5 experiments).

The observed effect is not due to a competition between IMP731 and the anti-LAG-3 17B4-FITC reagent since the binding of 17B4-FITC is not inhibited by a 3-fold excess of IMP731 (not shown). A putative internalization of the membrane LAG-3 induced by IMP731 was also excluded because the disappearance of activated T cells was also observed with an anti-CD25 antibody (see FIG. 16B). Note that half of CD25" cells are LAG-3$^-$ (in the CD4 subset, these cells are the natural Tregs) and are therefore not depleted. The depletion of CD25$^+$ cells versus LAG-3' cells is also minimized by the fact that many LAG-3' cells are CD25$^-$ (not shown).

CONCLUSIONS

IMP731 efficiently induced cell-mediated cytotoxicity of activated antigen-specific CD4 and CD8 human T cells at very low doses (1-10 ng/ml). From previous work we know that a concentration of 30 ng/ml IMP731 was measured at t=116 hr in the baboon injected with 0.1 mg/kg IMP731 (experiment showing a long-term suppression of DTH reaction). Therefore the concentration in the first few hours must have been much higher.

Based on this information, it is believed that a starting dose in human in the planned Phase Ia trial of 0.01 mg/kg could be pharmacologically active. It is possible that even such a very low dose could lead to >10 ng/ml serum concentration levels for a few hours and therefore be sufficient to deplete LAG-3$^+$ T cells in patients.

EXAMPLE 6

IMP731 DTH Studies in Baboons

IMP731 has been shown to be immunosuppressive after a single i.v. low dose (0.1 mg/kg) injection on a skin antigen-specific reaction (DTH) in baboon. This test is used as a surrogate in vivo assay for psoriasis inflammation. By continuing the DTH testing for five months after the injection of IMP731 it was possible to show that the immunosuppression was long-lasting corresponding to the "Campath Effect".

The choice of psoriasis as an initial indication is supported by the work showing that psoriatic skin is massively infiltrated with LAG-3$^+$ T cells compared to normal skin. The following describes the work which led to these results and conclusions.

IMP731 Suppresses DTH Reaction in Baboons

Figure 17:
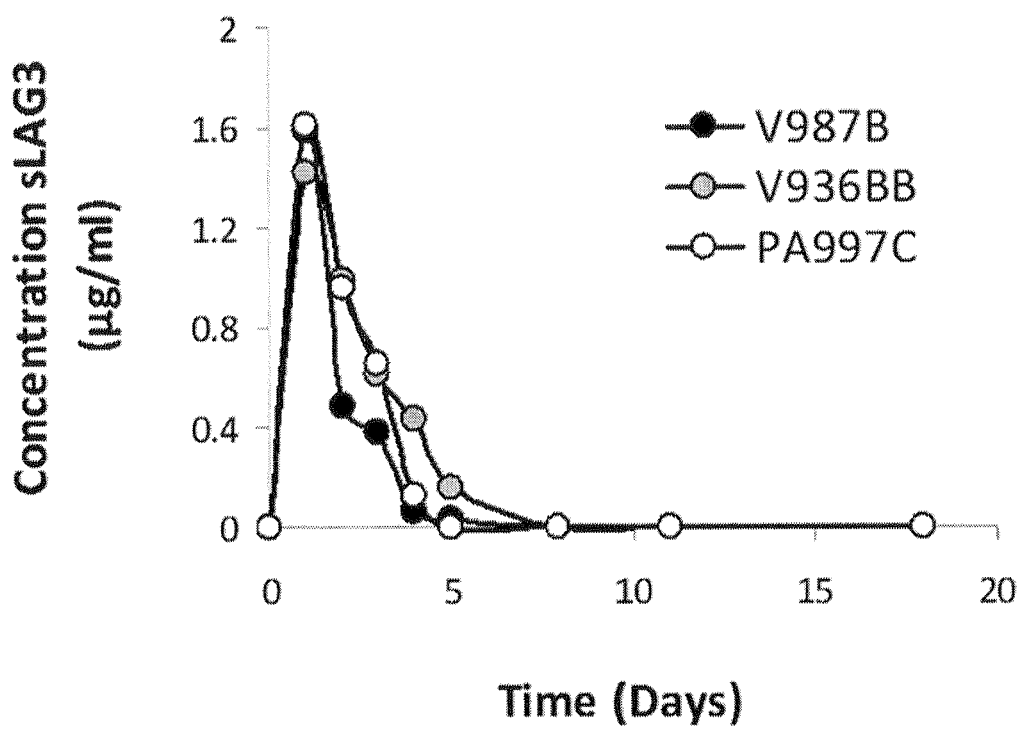
FIG. 17 depicts the pharmacokinetics of IMP731 injected into 3 baboons (0.1 mg/kg).

The half-life in 3 baboons injected (i.v.) with 0.1 mg/kg IMP731 showed similar pharmokinetic profiles with the following elimination half-life: 16, 21 and 31 hours (FIG. 17).

Delayed Type Hypersensitivity (DTH) reaction is an established model for skin inflammation (16-18). To assess the potency of IMP731 on skin tissue and their draining lymph nodes in baboons as a surrogate assay for the treatment of psoriasis lesions, 3 baboons were immunized with tuberculin and then their reactivity was assessed in a tuberculin-specific DTH reaction (see protocol in FIG. 18). In a DTH reaction the erythema (the reddened area of skin) measurement reflects an antigen-specific CD4 and CD8 T cell response over time.

Even a single dose as low as 0.1 mg/kg IMP731 is immunosuppressive as shown for Baboon #3 (FIG. 19) where the DTH is abrogated at a suboptimal dose (1:50 dilution) of tuberculin and is still inhibited in time and intensity at an optimal dose (1:1 dilution) of tuberculin. The relevance of the DTH results is clear. Both psoriasis and DTH are caused by antigen-specific LAG-3$^+$ activated T cells in the skin.

Decrease in LAG-3$^+$ T Cells in Lymph Nodes

To quantify the systemic deletion of circulating LAG-3$^+$ T cells following injection of IMP731, the number of LAG-3$^+$ T cells in the DTH site draining lymph nodes 3 days after the tuberculin injection was analyzed. The mean percentage of live LAG-3$^+$ cells in these immune-reactive lymph nodes was 3.5% for the first DTH and only 0.7% for the second DTH. This clearly indicates that IMP731 had killed 80% of LAG-3$^+$ cells in the antigen-reactive lymph node at day 3. This mechanism of action explains why the immunosuppressive effect on the DTH is long-lasting (see below).

IMP731 Still Suppresses DTH Reaction in Baboons Five Months after Injection

This immunosuppressive effect is sustained over time as a third, fourth and fifth DTH reaction performed up to five months after the IMP731 injection is still inhibited (FIG. 19). This clearly shows that the effect of antigen-specific immunosuppression is still as potent five months after the injection of IMP731. This effect is made even more striking by the fact that, whereas IMP731 can easily be detected in the blood in the few days following injection, two months later there are no detectable antibodies remaining.

Figure 18:
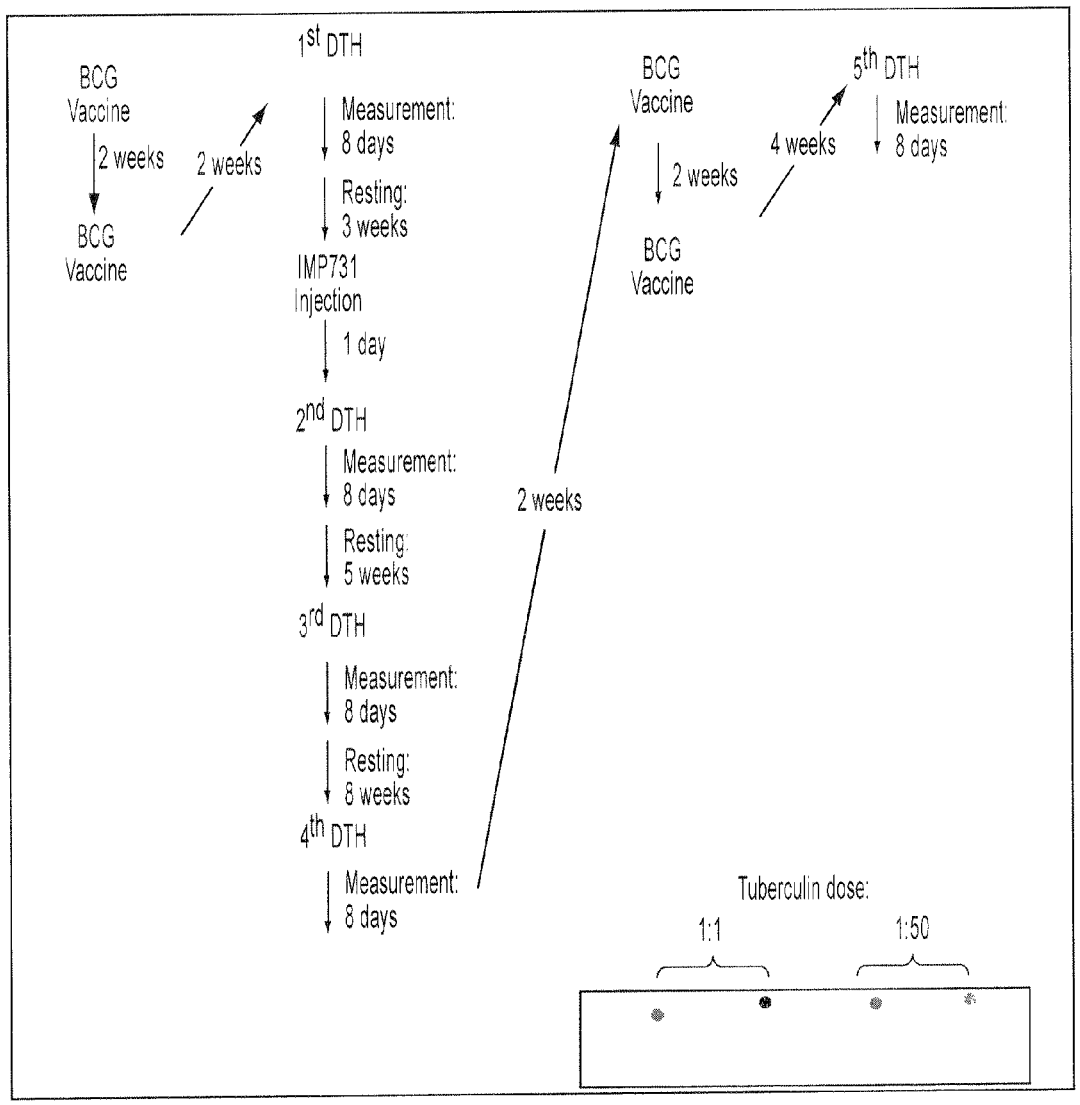
FIG. 18 depicts DTH reaction as a model for psoriasis inflammation in baboon. Two BCG vaccines were injected before the 5$^{th}$ DTH to test the long-term IMP731 depletion effect on tuberculin-specific memory T cells.

IMP731 Suppresses DTH Reaction for Five Months Even after Two Booster Immunizations This long duration of immunosuppressive effect was tested to determine whether it might be due to the deletion of tuberculin-specific memory T cells at the time of IMP731 injection. This is a possibility because CD45$^+$ memory T cells (in both CD4 and CD8 subsets) are LAG-3$^+$ in human. If so, the DTH would be suppressed following booster immunization. Accordingly, baboon #3 was injected with two BCG vaccines before performing the 5$^{th}$ DTH (FIG. 18). Remarkably, the DTH was still totally negative (FIG. 19).

It is established that memory T cells may take up to a year to recover from deletion in human (the "Campath Effect") (19). Therefore, it is likely that psoriasis patients can be treated with a low dose (e.g. 0.1 mg/kg) IMP731, which could be effective at deleting the activated memory T cells.

REFERENCES

1. Waldmann H. The new immunosuppression: just kill the T cell. Nat Med 2003; 9 (10): 1259.
2. Monk N J, Hargreaves R E, Marsh J E, et al. Fcdependent depletion of activated T cells occurs through CD40L-specific antibody rather than costimulation blockade. Nat Med 2003; 9 (10): 1275.
3. Andre P, Prasad K S, Denis C V, et al. CD40L stabilizes arterial thrombi by a beta3 integrin-dependent mechanism. Nat Med 2002; 8 (3): 247.
4. Avice M N, Sarfati M, Triebel F, Delespesse G, Demeure C E. Lymphocyte activation gene-3, a MHC class II ligand expressed on activated T cells, stimulates TNF-alpha and IL-12 production by monocytes and dendritic cells. J. Immunol. 1999; 162: 2748.
5. Andreae S, Piras F, Burdin N, Triebel F. Maturation and activation of dendritic cells induced by lymphocyte activation gene-3 (CD223). J Immunol 2002; 168 (8): 3874.
6. Andreae S, Buisson S, Triebel F. MHC class II signal transduction in human dendritic cells induced by a natural ligand, the LAG-3 protein (CD223). Blood 2003; 102 (6): 2130.
7. Triebel F. LAG-3: a regulator of T-cell and DC responses and its use in therapeutic vaccination. Trends Immunol 2003; 24 (12): 619.
8. Macon-Lemaitre L, Triebel F. The negative regulatory function of the lymphocyte-activation gene-3 co-receptor (CD223) on human T cells. Immunology 2005; 115 (2): 170.
9. Kohler and Milstein. Continuous cultures of fused cells secreting antibody of predefined specificity. Nature. 1975; 256(5517): 495-497.
10. Kozbor et al., 1985, in Monoclonal Antibodies and Cancer Therapy, Alan R. Liss, Inc., pp. 77-96.
11. Ono et al, Improved technique of heart transplantation in rats. J. Thorac. Cardiovasc. Surg. 57, 225-229.
12. Stasiuk et al, Collagen-induced arthritis in DBA/1 mice: Cytokine gene activation following immunization with type II collagen. Cellular Immunol. 1996; 173: 269-275.
13. Campbell et al, Collagen-induced arthritis in C57BL/6 (H-2b) mice: new insights into an important disease model of rheumatoid arthritis. Eur. J. Immunol. 2000; 30: 1568-1575.
14. Inglis et al, Collagen-induced arthritis in C57BL/6 is associated with a robust and sustained T-cell response to type II collagen. Arthritis Research & Therapy. 2007; 9: R113.
15. Hiroaki et al, A tumor necrosis factor receptor loop peptide mimic inhibits bone destruction to the same extent as anti-tumor necrosis factor monoclonal antibody in lurine collagen-induced arthritis. arthritis & Rheumatism. 2007; 56(4): 1164-1174.
16. Galli, S. J., and I. Hammel. 1984. Unequivocal delayed hypersensitivity in mast cell-deficient and beige mice. *Science* 226:710.
17. Lange-Asschenfeldt, B., W. Weninger, P. Velasco, T. R. Kyriakides, U. H. von Andrian, P. Bornstein, and M. Detmar. 2002. Increased and prolonged inflammation and angiogenesis in delayed-type hypersensitivity reactions elicited in the skin of thrombospondin-2-deficient mice. *Blood* 99:538.
18. Kunstfeld, R., S. Hirakawa, Y. K. Hong, V. Schacht, B. Lange-Asschenfeldt Velasco, C. Lin, E. Fiebiger, X. Wei, Y. Wu, D. Hicklin, P. Bohlen, and M. Detmar. 2004. Induction of cutaneous delayed-type hypersensitivity reactions in VEGF-A transgenic mice results in chronic skin inflammation associated with persistent lymphatic hyperplasia. *Blood* 104:1048., P.
19. Coles, A. J. et al. 2008 Alemtuzumab vs. interferon beta-1a in early multiple sclerosis. *N. Engl. J. Med.* 359: 1786.

All references, including publications, patent applications and patents cited herein are hereby incorporated by reference, as if each were individually and specifically indicated to be incorporated by reference and were set forth in its entirety herein.

The invention claimed is:

1. Monoclonal antibody IMP731 or a biologically active fragment thereof, wherein the monoclonal antibody IMP731 or the biologically active fragment thereof comprises a light chain kappa region as set forth in amino acids 21 to 240 of SEQ ID NO:13 and a heavy chain gamma region as set forth in amino acids 20 to 465 of SEQ ID NO:16, and wherein the monoclonal antibody IMP731 or biologically active fragment thereof comprises an Fc fragment from human IgG1, human IgM, or mouse IgG2a and a Fab fragment that binds LaG-3 protein, and wherein said moloclonal antibody IMP731 or biologically active fragment thereof is capable of depleting LAG-3+ activated T cells in a complement dependent cytotoxicity (CDC) assay, or in an antibody-dependent cell cytotoxicity (ADCC) assay, or both.

2. A pharmaceutical composition comprising the monoclonal antibody IMP731 or biologically active fragment thereof of claim 1.

3. An antibody or fragment thereof comprising a kappa light chain (variable region) polypeptide encoded by a nucleic acid molecule as set forth in SEQ ID NO: 8 and a gamma heavy chain (variable region) polypeptide encoded by a nucleic acid molecule as set forth in SEQ ID NO: 10, wherein said antibody or fragment thereof comprises an fc fragment from human IgG1, human IgM, or mouse IgG2a and an Fab fragment that binds LAG-3 protein, and wherein said antibody or fragment thereof is capable of depleting LAG-3+ activated T cells in a complement dependent cytotoxicity (CDC) assay, or in an antibody-dependent cell cytotoxicity (ADCC) assay, or both.

4. The antibody or fragment thereof of claim 3, comprising two polypeptides having the following amino acid sequences:

```
                                              (SEQ ID NO: 9)
Q S P K L L V Y F A S T R D S G V P D R F I G S

G S G T D F T L T I S S V Q A E D L A D Y F C L

Q H F G T P P T F G G G T K L E I K R; and (SEQ ID NO: 11)
Q V Q L K E S G P G L V A P S Q S L S I T C T V

S G F S L T A Y G V N W V R Q P P G K G L E W L

G M I W D D G S T D Y N S A L K S R L S I S K D

N S K S Q V F L K M N S L Q T D D T A R Y Y C A

R E G D V A F D Y W G Q G T T L T V S S.
```

5. An antibody or a biologically active fragment thereof, wherein said antibody or biologically active fragment thereof comprises a light chain variable region comprising a CDR-L1 having the amino acid sequence as set forth in SEQ ID NO: 17, a CDR-L2 having the amino acid sequence of FAS, and a CDR-L3 having the amino acid sequence as set forth in SEQ ID NO: 18 and a heavy chain variable region comprising a CDR-H1 having the amino acid sequence as set forth in SEQ ID NO: 19, a CDR-H2 having the amino acid sequence as set forth in SEQ ID NO: 20, and a CDR-H3 having the amino acid sequence as set forth in SEQ ID NO: 21.

* * * * *